(12) United States Patent
Isola et al.

(10) Patent No.: US 6,942,970 B2
(45) Date of Patent: Sep. 13, 2005

(54) IDENTIFYING SUBJECTS SUITABLE FOR TOPOISOMERASE II INHIBITOR TREATMENT

(75) Inventors: Jorma Isola, Pirkkala (FI); Minna Tanner, Tampere (FI); Tero Jarvinen, Tampere (FI); Zuo-Rong Shi, Pirkkala (FI); Rina Wu, Tampere (FI)

(73) Assignee: Zymed Laboratories, Inc., So. San Francisco, CA (US)

( * ) Notice: Subject to any disclaimer, the term of this patent is extended or adjusted under 35 U.S.C. 154(b) by 0 days.

(21) Appl. No.: 09/952,851

(22) Filed: Sep. 14, 2001

(65) Prior Publication Data

US 2003/0134279 A1 Jul. 17, 2003

(Under 37 CFR 1.47)

Related U.S. Application Data

(60) Provisional application No. 60/232,660, filed on Sep. 14, 2000.

(51) Int. Cl.[7] .......................... C12Q 1/68; C12P 19/34; C07H 21/04

(52) U.S. Cl. ..................... 435/6; 435/91.2; 536/23.2; 536/23.5; 536/24.31

(58) Field of Search ................... 435/6, 91.2, 233; 536/23.2, 23.5, 24.31; 424/9.2, 138.1; 530/350; 514/34

(56) References Cited

U.S. PATENT DOCUMENTS

| | | |
|---|---|---|
| 5,643,761 A | 7/1997 | Fisher et al. ............... 435/91.1 |
| 5,750,340 A | 5/1998 | Kim et al. .................... 435/6 |
| 6,070,126 A | 5/2000 | Kokolus et al. ............. 702/19 |

OTHER PUBLICATIONS

Tanner, M.M. et al. Topoisomerase IIalpha amplification and deletion predict response to chemotherapy in breast cancer. Proceedings of the American Association for Cancer Research 41:802 (Mar. 2000).*

Jarvinen, T.A.H. et al. Amplification and deletion of topoisomerase IIalpha associate with erbB-2 amplification and affect sensitivity to topoisomerase II inhibitor doxorubicin in breast cancer. American Journal of Pathology 156(e):839–847 (Mar. 2000).*

Aileen Constans, "No FISHing", The Scientist, vol. 14, Issue 15 (2000).

Spot–Light™ HER2 DNA Probe, An SPT™ Probe for In Situ Hybridization, Zymed® Laboratories, Inc., Product Information Sheet, distributed beginning in Oct. 1999.

Spot–Light™ CISH Detection Kit, Zymed® Laboratories Inc., Product Information Sheet, distributed beginning in Oct. 1999.

Spot–Light™ Cell Pretreatment Reagent for Enzyme Reagent for Cell Preparations prior to ISH Detection, Zymed® Laboratories Inc., Product Information Sheet, distributed beginning in Oct. 1999.

Spot–Light™ Tissue Pretreatment Kit for Enzyme and Heat Pretreatment of FFPE Tissue prior to ISH, Zymed® Laboratories Inc., Product Information Sheet, distributed beginning in Oct. 1999.

Allred et al., Mod. Pathol., 11:155–168 [1998].

Kuo et al., Am. J. Hum. Genet., 49:112–119 (1991).

(Continued)

Primary Examiner—Diana B. Johannsen
(74) Attorney, Agent, or Firm—Medlen & Carroll, LLP

(57) ABSTRACT

The present invention provides methods for diagnosing and treating cancer, and in particular methods for determining the susceptibility of subjects suspected of having breast cancer (or known to have breast cancer) to treatment with topoisomerase II inhibitors. The present invention also provides in situ hybridization probes for specifically detecting topoII$\alpha$ gene sequences.

11 Claims, 2 Drawing Sheets

Topoisomerase II$\alpha$ gene status does not correlate with immunohistochemistry

OTHER PUBLICATIONS

McNeil, C., *J. Natl. Cancer Inst.*, 91:100, [1999].
Tetu et al., *Mod. Pathol.*, 11:823 [1998].
Clahsen et al., *J. Clin. Oncol.*, 16:470 [1998].
Thor et al., *J. Natl. Cancer Inst.*, 90:1346 [1998].
Shak. S., *Semin. Oncol.*, 6:71 [1999].
Jiminez et al., *Mod. Pathol.*, 13:37 [2000].
Mitchell, M.S., *Semin. Oncol.*, 26:108 [1999].
Smith et al., *Oncogene*, 8:933 (1993).
Murphy et al., *Int. J. Cancer*, 64:18–26 (1996).
Hoare et al., *Br. J. Cancer*, 75:275 (1997).
Jarvinen, et al., *British Journal of Cancer*, 77(12):2267 (1998).
Tanner et al., *Cancer Res.*, 54:4257 [1994].
Heiskanen et al., *Genomics*, 30:31 [1995].
Kellner et al., *J. Hitochem. Cytochem*, 45:251 [1997].
Joensuu et al., *J. Clin. Oncol.*, 16:3720 [1998].
Miller et al., *Cancer*, 47:207–214 [1981].
Grancberg, et al., *Am. J. Clin. Pathol.*, 113:675 [2000].
Davison et al., Technical Advance. Substracted Unique sequence in situ hybridization Experimental And Diagnostic Applications, Am. J. Pathol., 153:1401–1409 (1998).
Jossart et al., A novel multicolor hybridization scheme applied to localization of a transcribed sequence (D 10S 170/H4) and deletion mapping in the thyroid cancer cell line TPC–1. Cytogenet. Cell. Genet., 75:254–257 (1996).
Pauletti et al., Assessment of methods for tissue–based detection of the Her–2/neu alteration in human breast cancer: A direct comparison of fluorescence in situ hybridization and immunohistochemistry, J. Clin. Oncology, 18:3651–3664 (2000).
Miyagi et al., Cloning and characterization of an interstitial deletion at chromosome 11p15 in a sporadic breast cancer, Human Molecular Genetics, 1:705–708 (1992).

* cited by examiner

FIGURE 2

A. SEQ ID NO:9 (3' end of Exemplary topoIIa probe sequence)

GAAGATACATCCAAANTCCAGCCTACGCAACAGAGCAGGATTCAGTCTCAAAAAAAGAAAAAAAGAAAAGAAAACGTTC
CCCACCCCATCTCCTTCCTTGATCATCACTGGACCCTGTTCTGCCACCAACTTGCGTGAACTTGGAGTTTGACTGACCT
TAGCTGTAACATGGAGGTAGATCATCTCCACCCATCCTACCTCTTGAAGCTCTTGTGAGAGTAAAATGAATGGAGAAGA
GTAGTTCTGCTCCCAATGCCAGACATGTGCCCTGTTCAGCAAGCCCAAGAGGAGAAAAGGTGCCAGGACACAGAGGCAG
GAGTGCAGGAGAGGCCGGACAAACCCACGCAACATGCCTGGGATGAAGCATGAGTGCAGGTGAGTGTGGGAATCTGCAA
AGGTTGCCAGA

B. SEQ ID NO:10 (5' end of Exemplary topoIIa probe sequence)

GCNGNNGNCAAGCCTNCCAAGGTAGGNTTCCGANNGGCGGCCGCCTGGCCGNCNACATTTAAGNNGACACTATAGAAGG
ATCGTNGNATTGTTGCNTCCCTCTTTACNGGCNCTATGGCTCNATTTTGTTNGNTACTGAGGGGTAAAAGATAAATGTT
TACCNTNACCTAAAATTGGNTTNNGGCCTCTAAAGGAACCNGAGGCTTAAANGAATTATNGGCTTTGGAAGCNGGCCTT
CAAATTACTGCGCTAATTTATATTTTTCATTAAAAACTCAGCTGGCCTCNTCTATATAGNTGTCTTCCCTGGCCNTGAA
ACCCNANTGTTTCGCCANAAANGATTTTAAAATTAAGGGGTCATAATTCCCNCCCCATGATGTGTGGATTAATGGTAAG
AAGGATGCCCAGAACGTTNTNTTCTTAGGTTGAACGAANANAAAAGTNAAANAGTNGGGCTCTGGNTTCTCNCCTTTGA
AGCCNCNCAATTCGNGAGATACTATGCTGAACCNTAGTTTTTCTTTATATAGGGGNGTNGAACTTTACCCTCAAAATCA
NTANNTCAGCACATCAAGGANATTNTGGATCNTNGGNTCTTCNCTGNCNCCNANATGCTGGGACCNNNNACCTTGCATN
AACAGTTTGCTTTNGTNCCTNTGCANAGGGNTGNGCNTTTCCAANAGGGNAAGGCAANGGCCTAACATCATACCTGGGN
GCCNAGNAANCCNAAANACNGGGAAGGNCTCNCNTACCC

SEQUENCE LISTING

<160> NUMBER OF SEQ ID NOS: 12

<210> SEQ ID NO 1
<211> LENGTH: 22
<212> TYPE: DNA
<213> ORGANISM: Artificial
<220> FEATURE:
<223> OTHER INFORMATION: Synthetic

<400> SEQUENCE: 1
gcctccctaa cctgattggt tt                                              22

<210> SEQ ID NO 2
<211> LENGTH: 22
<212> TYPE: DNA
<213> ORGANISM: Artificial
<220> FEATURE:
<223> OTHER INFORMATION: Synthetic

<400> SEQUENCE: 2
ctgaagaacc ctgaaagcga ct                                              22

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
ctggctccga tgtatttgat g                                               21

<210> SEQ ID NO 4
<211> LENGTH: 22
<212> TYPE: DNA
<213> ORGANISM: Artificial
<220> FEATURE:
<223> OTHER INFORMATION: Synthetic

<400> SEQUENCE: 4
cctgcccata agtctctctg ct                                              22

<210> SEQ ID NO 5
<211> LENGTH: 20
<212> TYPE: DNA
<213> ORGANISM: Artificial
<220> FEATURE:
<223> OTHER INFORMATION: Synthetic

<400> SEQUENCE: 5
gattagcctg ccctctttgg                                                 20

<210> SEQ ID NO 6
<211> LENGTH: 20
<212> TYPE: DNA
<213> ORGANISM: Artificial
<220> FEATURE:
<223> OTHER INFORMATION: Synthetic

<400> SEQUENCE: 6
cagaagggag gcagacagtc                                                 20

<210> SEQ ID NO 7
<211> LENGTH: 21

```
<212> TYPE: DNA
<213> ORGANISM: Artificial
<220> FEATURE:
<223> OTHER INFORMATION: Synthetic

<400> SEQUENCE: 7
gctcatggtg tcaggaggat g                                              21

<210> SEQ ID NO 8
<211> LENGTH: 21
<212> TYPE: DNA
<213> ORGANISM: Artificial
<220> FEATURE:
<223> OTHER INFORMATION: Synthetic

<400> SEQUENCE: 8
gcaggaatag gtgggatgga g                                              21

<210> SEQ ID NO 9
<211> LENGTH: 406
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (16)..(16)
<223> OTHER INFORMATION: The n at this position can be a, c, t, or g.

<400> SEQUENCE: 9
gaagatacat ccaaantcca gcctacgcaa cagagcagga ttcagtctca aaaaaagaaa      60
aaaagaaaag aaaacgttcc ccaccccatc tccttccttg atcatcactg gaccctgttc    120
tgccaccaac ttgcgtgaac ttggagtttg actgaccttta gctgtaacat ggaggtagat    180
catctccacc catcctacct cttgaagctc ttgtgagagt aaaatgaatg gagaagagta    240
gttctgctcc caatgccaga catgtgccct gttcagcaag cccaagagga gaaaggtgc    300 caggacacag aggcaggagt gcaggagagg ccggacaaac ccacgcaaca tgcctgggat    360
gaagcatgag tgcaggtgag tgtgggaatc tgcaaaggtt gccaga                   406

<210> SEQ ID NO 10
<211> LENGTH: 750
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The n at this position can be a, c, t, or g.
<220> FEATURE:
<221> NAME/KEY: misc_feature
<222> LOCATION: (5)..(6)
<223> OTHER INFORMATION: The n at this position can be a, c, t, or g.
<220> FEATURE:
<221> NAME/KEY: misc_feature
<222> LOCATION: (8)..(8)
<223> OTHER INFORMATION: The n at this position can be a, c, t, or g.
<220> FEATURE:
<221> NAME/KEY: misc_feature
<222> LOCATION: (16)..(16)
<223> OTHER INFORMATION: The n at this position can be a, c, t, or g.
<220> FEATURE:
<221> NAME/KEY: misc_feature
<222> LOCATION: (27)..(27)
<223> OTHER INFORMATION: The n at this position can be a, c, t, or g.
<220> FEATURE:
<221> NAME/KEY: misc_feature
<222> LOCATION: (34)..(35)
```

-continued

```
<223> OTHER INFORMATION: The n at this position can be a, c, t, or g.
<220> FEATURE:
<221> NAME/KEY: misc_feature
<222> LOCATION: (52)..(52)
<223> OTHER INFORMATION: The n at this position can be a, c, t, or g.
<220> FEATURE:
<221> NAME/KEY: misc_feature
<222> LOCATION: (54)..(54)
<223> OTHER INFORMATION: The n at this position can be a, c, t, or g.
<220> FEATURE:
<221> NAME/KEY: misc_feature
<222> LOCATION: (64)..(65)
<223> OTHER INFORMATION: The n at this position can be a, c, t, or g.
<220> FEATURE:
<221> NAME/KEY: misc_feature
<222> LOCATION: (85)..(85)
<223> OTHER INFORMATION: The n at this position can be a, c, t, or g.
<220> FEATURE:
<221> NAME/KEY: misc_feature
<222> LOCATION: (87)..(87)
<223> OTHER INFORMATION: The n at this position can be a, c, t, or g.
<220> FEATURE:
<221> NAME/KEY: misc_feature
<222> LOCATION: (96)..(96)
<223> OTHER INFORMATION: The n at this position can be a, c, t, or g.
<220> FEATURE:
<221> NAME/KEY: misc_feature
<222> LOCATION: (108)..(108)
<223> OTHER INFORMATION: The n at this position can be a, c, t, or g.
<220> FEATURE:
<221> NAME/KEY: misc_feature
<222> LOCATION: (112)..(112)
<223> OTHER INFORMATION: The n at this position can be a, c, t, or g.
<220> FEATURE:
<221> NAME/KEY: misc_feature
<222> LOCATION: (122)..(122)
<223> OTHER INFORMATION: The n at this position can be a, c, t, or g.
<220> FEATURE:
<221> NAME/KEY: misc_feature
<222> LOCATION: (131)..(131)
<223> OTHER INFORMATION: The n at this position can be a, c, t, or g.
<220> FEATURE:
<221> NAME/KEY: misc_feature
<222> LOCATION: (133)..(133)
<223> OTHER INFORMATION: The n at this position can be a, c, t, or g.
<220> FEATURE:
<221> NAME/KEY: misc_feature
<222> LOCATION: (163)..(163)
<223> OTHER INFORMATION: The n at this position can be a, c, t, or g.
<220> FEATURE:
<221> NAME/KEY: misc_feature
<222> LOCATION: (165)..(165)
<223> OTHER INFORMATION: The n at this position can be a, c, t, or g.
<220> FEATURE:
<221> NAME/KEY: misc_feature
<222> LOCATION: (178)..(178)
<223> OTHER INFORMATION: The n at this position can be a, c, t, or g.
<220> FEATURE:
<221> NAME/KEY: misc_feature
<222> LOCATION: (181)..(182)
<223> OTHER INFORMATION: The n at this position can be a, c, t, or g.
<220> FEATURE:
<221> NAME/KEY: misc_feature
<222> LOCATION: (199)..(199)
<223> OTHER INFORMATION: The n at this position can be a, c, t, or g.
<220> FEATURE:
<221> NAME/KEY: misc_feature
<222> LOCATION: (210)..(210)
<223> OTHER INFORMATION: The n at this position can be a, c, t, or g.
<220> FEATURE:
<221> NAME/KEY: misc_feature
<222> LOCATION: (218)..(218)
<223> OTHER INFORMATION: The n at this position can be a, c, t, or g.
<220> FEATURE:
<221> NAME/KEY: misc_feature
<222> LOCATION: (231)..(231)
<223> OTHER INFORMATION: The n at this position can be a, c, t, or g.
<220> FEATURE:
<221> NAME/KEY: misc_feature
```

```
<222> LOCATION: (287)..(287)
<223> OTHER INFORMATION: The n at this position can be a, c, t, or g.
<220> FEATURE:
<221> NAME/KEY: misc_feature
<222> LOCATION: (297)..(297)
<223> OTHER INFORMATION: The n at this position can be a, c, t, or g.
<220> FEATURE:
<221> NAME/KEY: misc_feature
<222> LOCATION: (312)..(312)
<223> OTHER INFORMATION: The n at this position can be a, c, t, or g.
<220> FEATURE:
<221> NAME/KEY: misc_feature
<222> LOCATION: (321)..(321)
<223> OTHER INFORMATION: The n at this position can be a, c, t, or g.
<220> FEATURE:
<221> NAME/KEY: misc_feature
<222> LOCATION: (323)..(323)
<223> OTHER INFORMATION: The n at this position can be a, c, t, or g.
<220> FEATURE:
<221> NAME/KEY: misc_feature
<222> LOCATION: (334)..(334)
<223> OTHER INFORMATION: The n at this position can be a, c, t, or g.
<220> FEATURE:
<221> NAME/KEY: misc_feature
<222> LOCATION: (338)..(338)
<223> OTHER INFORMATION: The n at this position can be a, c, t, or g.
<220> FEATURE:
<221> NAME/KEY: misc_feature
<222> LOCATION: (368)..(368)
<223> OTHER INFORMATION: The n at this position can be a, c, t, or g.
<220> FEATURE:
<221> NAME/KEY: misc_feature
<222> LOCATION: (414)..(414)
<223> OTHER INFORMATION: The n at this position can be a, c, t, or g.
<220> FEATURE:
<221> NAME/KEY: misc_feature
<222> LOCATION: (416)..(416)
<223> OTHER INFORMATION: The n at this position can be a, c, t, or g.
<220> FEATURE:
<221> NAME/KEY: misc_feature
<222> LOCATION: (434)..(434)
<223> OTHER INFORMATION: The n at this position can be a, c, t, or g.
<220> FEATURE:
<221> NAME/KEY: misc_feature
<222> LOCATION: (436)..(436)
<223> OTHER INFORMATION: The n at this position can be a, c, t, or g.
<220> FEATURE:
<221> NAME/KEY: misc_feature
<222> LOCATION: (443)..(443)
<223> OTHER INFORMATION: The n at this position can be a, c, t, or g.
<220> FEATURE:
<221> NAME/KEY: misc_feature
<222> LOCATION: (447)..(447)
<223> OTHER INFORMATION: The n at this position can be a, c, t, or g.
<220> FEATURE:
<221> NAME/KEY: misc_feature
<222> LOCATION: (451)..(451)
<223> OTHER INFORMATION: The n at this position can be a, c, t, or g.
<220> FEATURE:
<221> NAME/KEY: misc_feature
<222> LOCATION: (461)..(461)
<223> OTHER INFORMATION: The n at this position can be a, c, t, or g.
<220> FEATURE:
<221> NAME/KEY: misc_feature
<222> LOCATION: (467)..(467)
<223> OTHER INFORMATION: The n at this position can be a, c, t, or g.
<220> FEATURE:
<221> NAME/KEY: misc_feature
<222> LOCATION: (479)..(479)
<223> OTHER INFORMATION: The n at this position can be a, c, t, or g.
<220> FEATURE:
<221> NAME/KEY: misc_feature
<222> LOCATION: (481)..(481)
<223> OTHER INFORMATION: The n at this position can be a, c, t, or g.
<220> FEATURE:
<221> NAME/KEY: misc_feature
<222> LOCATION: (489)..(489)
<223> OTHER INFORMATION: The n at this position can be a, c, t, or g.
<220> FEATURE:
```

-continued

```
<221> NAME/KEY: misc_feature
<222> LOCATION: (508)..(508)
<223> OTHER INFORMATION: The n at this position can be a, c, t, or g.
<220> FEATURE:
<221> NAME/KEY: misc_feature
<222> LOCATION: (530)..(530)
<223> OTHER INFORMATION: The n at this position can be a, c, t, or g.
<220> FEATURE:
<221> NAME/KEY: misc_feature
<222> LOCATION: (533)..(533)
<223> OTHER INFORMATION: The n at this position can be a, c, t, or g.
<220> FEATURE:
<221> NAME/KEY: misc_feature
<222> LOCATION: (554)..(554)
<223> OTHER INFORMATION: The n at this position can be a, c, t, or g.
<220> FEATURE:
<221> NAME/KEY: misc_feature
<222> LOCATION: (557)..(558)
<223> OTHER INFORMATION: The n at this position can be a, c, t, or g.
<220> FEATURE:
<221> NAME/KEY: misc_feature
<222> LOCATION: (574)..(574)
<223> OTHER INFORMATION: The n at this position can be a, c, t, or g.
<220> FEATURE:
<221> NAME/KEY: misc_feature
<222> LOCATION: (578)..(578)
<223> OTHER INFORMATION: The n at this position can be a, c, t, or g.
<220> FEATURE:
<221> NAME/KEY: misc_feature
<222> LOCATION: (585)..(585)
<223> OTHER INFORMATION: The n at this position can be a, c, t, or g.
<220> FEATURE:
<221> NAME/KEY: misc_feature
<222> LOCATION: (587)..(587)
<223> OTHER INFORMATION: The n at this position can be a, c, t, or g.
<220> FEATURE:
<221> NAME/KEY: misc_feature
<222> LOCATION: (590)..(590)
<223> OTHER INFORMATION: The n at this position can be a, c, t, or g.
<220> FEATURE:
<221> NAME/KEY: misc_feature
<222> LOCATION: (596)..(596)
<223> OTHER INFORMATION: The n at this position can be a, c, t, or g.
<220> FEATURE:
<221> NAME/KEY: misc_feature
<222> LOCATION: (600)..(600)
<223> OTHER INFORMATION: The n at this position can be a, c, t, or g.
<220> FEATURE:
<221> NAME/KEY: misc_feature
<222> LOCATION: (602)..(602)
<223> OTHER INFORMATION: The n at this position can be a, c, t, or g.
<220> FEATURE:
<221> NAME/KEY: misc_feature
<222> LOCATION: (605)..(605)
<223> OTHER INFORMATION: The n at this position can be a, c, t, or g.
<220> FEATURE:
<221> NAME/KEY: misc_feature
<222> LOCATION: (607)..(607)
<223> OTHER INFORMATION: The n at this position can be a, c, t, or g.
<220> FEATURE:
<221> NAME/KEY: misc_feature
<222> LOCATION: (619)..(622)
<223> OTHER INFORMATION: The n at this position can be a, c, t, or g.
<220> FEATURE:
<221> NAME/KEY: misc_feature
<222> LOCATION: (632)..(632)
<223> OTHER INFORMATION: The n at this position can be a, c, t, or g.
<220> FEATURE:
<221> NAME/KEY: misc_feature
<222> LOCATION: (646)..(646)
<223> OTHER INFORMATION: The n at this position can be a, c, t, or g.
<220> FEATURE:
<221> NAME/KEY: misc_feature
<222> LOCATION: (649)..(649)
<223> OTHER INFORMATION: The n at this position can be a, c, t, or g.
<220> FEATURE:
<221> NAME/KEY: misc_feature
<222> LOCATION: (653)..(653)
<223> OTHER INFORMATION: The n at this position can be a, c, t, or g.
```

```
<220> FEATURE:
<221> NAME/KEY: misc_feature
<222> LOCATION: (658)..(658)
<223> OTHER INFORMATION: The n at this position can be a, c, t, or g.
<220> FEATURE:
<221> NAME/KEY: misc_feature
<222> LOCATION: (663)..(663)
<223> OTHER INFORMATION: The n at this position can be a, c, t, or g.
<220> FEATURE:
<221> NAME/KEY: misc_feature
<222> LOCATION: (666)..(666)
<223> OTHER INFORMATION: The n at this position can be a, c, t, or g.
<220> FEATURE:
<221> NAME/KEY: misc_feature
<222> LOCATION: (669)..(669)
<223> OTHER INFORMATION: The n at this position can be a, c, t, or g.
<220> FEATURE:
<221> NAME/KEY: misc_feature
<222> LOCATION: (677)..(677)
<223> OTHER INFORMATION: The n at this position can be a, c, t, or g.
<220> FEATURE:
<221> NAME/KEY: misc_feature
<222> LOCATION: (682)..(682)
<223> OTHER INFORMATION: The n at this position can be a, c, t, or g.
<220> FEATURE:
<221> NAME/KEY: misc_feature
<222> LOCATION: (690)..(690)
<223> OTHER INFORMATION: The n at this position can be a, c, t, or g.
<220> FEATURE:
<221> NAME/KEY: misc_feature
<222> LOCATION: (711)..(711)
<223> OTHER INFORMATION: The n at this position can be a, c, t, or g.
<220> FEATURE:
<221> NAME/KEY: misc_feature
<222> LOCATION: (715)..(715)
<223> OTHER INFORMATION: The n at this position can be a, c, t, or g.
<220> FEATURE:
<221> NAME/KEY: misc_feature
<222> LOCATION: (718)..(718)
<223> OTHER INFORMATION: The n at this position can be a, c, t, or g.
<220> FEATURE:
<221> NAME/KEY: misc_feature
<222> LOCATION: (721)..(721)
<223> OTHER INFORMATION: The n at this position can be a, c, t, or g.
<220> FEATURE:
<221> NAME/KEY: misc_feature
<222> LOCATION: (724)..(724)
<223> OTHER INFORMATION: The n at this position can be a, c, t, or g.
<220> FEATURE:
<221> NAME/KEY: misc_feature
<222> LOCATION: (728)..(728)
<223> OTHER INFORMATION: The n at this position can be a, c, t, or g.
<220> FEATURE:
<221> NAME/KEY: misc_feature
<222> LOCATION: (731)..(731)
<223> OTHER INFORMATION: The n at this position can be a, c, t, or g.
<220> FEATURE:
<221> NAME/KEY: misc_feature
<222> LOCATION: (739)..(739)
<223> OTHER INFORMATION: The n at this position can be a, c, t, or g.
<220> FEATURE:
<221> NAME/KEY: misc_feature
<222> LOCATION: (743)..(743)
<223> OTHER INFORMATION: The n at this position can be a, c, t, or g.
<220> FEATURE:
<221> NAME/KEY: misc_feature
<222> LOCATION: (745)..(745)
<223> OTHER INFORMATION: The n at this position can be a, c, t, or g.

<400> SEQUENCE: 10
gcngnngnca agcctnccaa ggtaggnttc cgannggcgg ccgcctggcc gncnacattt      60
aagnngacac tatagaagga tcgtngnatt gttgcntccc tctttacngg cnctatggct     120
cnattttgtt ngntactgag gggtaaaaga taaatgttta ccntnaccta aaattggntt     180
nnggcctcta aaggaaccng aggcttaaan gaattatngg ctttggaagc nggccttcaa     240
```

-continued

```
attactgcgc taatttatat ttttcattaa aaactcagct ggcctcntct atatagntgt    300
cttccctggc cntgaaaccc nantgtttcg ccanaaanga ttttaaaatt aagggtcat    360 aattcccncc ccatgatgtg tggattaatg gtaagaagga tgcccagaac gttntnttct    420
taggttgaac gaananaaaa gtnaaanagt ngggctctgg nttctcncct ttgaagccnc    480
ncaattcgng agatactatg ctgaaccnta gttttctttt atatagggg gtngaactttt   540 accctcaaaa tcantanntc agcacatcaa gganattntg gatcntnggn tcttcnctgn   600
cnccnanatg ctgggaccnn nnaccttgca tnaacagttt gctttngtnc ctntgcanag   660
ggntgngcnt ttccaanagg gnaaggcaan ggcctaacat catacctggg ngccnagnaa   720
nccnaaanac ngggaaggnc tcncntaccc                                    750
```

<210> SEQ ID NO 11
<211> LENGTH: 22
<212> TYPE: DNA
<213> ORGANISM: Artificial
<220> FEATURE:
<223> OTHER INFORMATION: Synthetic

<400> SEQUENCE: 11
gcctccctaa cctgattggt ta                                            22

<210> SEQ ID NO 12
<211> LENGTH: 22
<212> TYPE: DNA
<213> ORGANISM: Artificial
<220> FEATURE:
<223> OTHER INFORMATION: Synthetic

<400> SEQUENCE: 12
ctcaagaacc ctgaaagcga ct                                            22

IDENTIFYING SUBJECTS SUITABLE FOR TOPOISOMERASE II INHIBITOR TREATMENT

The present application claims priority to Provisional Application Ser. No. 60/232,660, filed Sep. 14, 2000, hereby incorporated by reference.

FIELD OF THE INVENTION

The present invention relates to methods for diagnosing and treating cancer, and in particular methods for determining the susceptibility of subjects suspected of having breast cancer to treatment with topoisomerase II inhibitors. The present invention also relates to in situ hybridization probes for specifically detecting topoIIα gene sequences.

BACKGROUND OF THE INVENTION

Breast cancer is the most common female malignancy in most industrialized countries, as it is estimated to affect about 10% of the female population during their lifespan. Although its mortality has not increased along with its incidence, due to earlier diagnosis and improved treatment, it is still one of the predominant causes of death in middle-aged women.

The primary treatment for breast cancer is surgery, either alone or combined with systemic adjuvant therapy (hormonal or cytotoxic) and/or post-operative irradiation. Most patients are cured with these treatments, but approximately 25–30% of women with node-negative disease and at least 50–60% of women with positive nodes, who appear to be disease-free after locoregional treatment, will relapse and need treatment for their metastatic disease. Thus, metastatic breast cancer is a significant and growing problem in oncology.

Approximately 30 to 40% of women with operable breast cancer eventually develop distant metastases. Metastatic breast cancer is commonly treated with anthracyclins, such as doxorubicin and epirubicin, which act via inhibiting the topoisomerase II (topoII) enzyme in cancer cells. A favorable response to topoII inhibitor-based chemotherapy improves post-chemotherapy survival and has a positive effect on the quality of life.

The response of patients to topoisomerase II inhibitors is widely variable. In addition, only 5 to 10% of breast cancer patients with overtly metastatic disease achieve complete clinical remission. In 30 to 50% of such cases, the response is partial, and the duration of response typically ranges from 6 to 24 months. In the remaining patients, either no objective response is detected, or the disease progresses despite ongoing treatment. The variation in the response rates highlights the need to identify patients who are likely to respond, and those who will obtain little or no benefit from a particular type of therapy or therapeutic regimen. Patients who are unlikely to respond to topoisomerase II inhibitors could be treated with alternative chemotherapeutic agents, such as taxanes, vinorelbine, or trastuzumab (HERCEPTIN). Unfortunately, the predictability of response is hindered by a lack of reliable markers. Indeed, conventional prognostic markers, such as the primary tumor size, axillary node status, and the histological grade of the tumor have not proven to be useful in the prediction of response to chemotherapy (Allred et al., *Mod. Pathol.*, 11:155–168 [1998]). Also, controversial results have been reported for the use of S-phase fraction size, estrogen receptor characteristics, progesterone receptor characteristics or p53 expression, as predictors of patient response to chemotherapy. As such, there is a need for reliable markers for detecting patients with, or susceptible to, metastatic breast cancer. Indeed, reliable markers are urgently needed in order to facilitate the implementation of appropriate therapeutic regimens for these patients.

SUMMARY OF THE INVENTION

The present invention provides methods for diagnosing and treating cancer, and in particular methods for determining the susceptibility of subjects suspected of having breast cancer to treatment with topoisomerase II inhibitors. The present invention also provides in situ hybridization probes and kits for specifically detecting topoIIα gene sequences.

In some embodiments, the present invention provides methods for identifying a candidate for topoisomerase II inhibitor treatment, comprising: a) providing a candidate subject suspected of having cancer cells; b) detecting a copy number for both HER-2/neu and topoIIα in the cancer cells; and c) identifying the candidate subject as being suitable for treatment with a topoisomerase II inhibitor, wherein the identifying comprises demonstrating amplification of the copy number for both HER-2/neu and topoIIα. In some embodiments, the candidate subject has cancer cells. In other embodiments, the candidate subject has been previously diagnosed as having cancer cells from diseases including, but not limited to, leukemia, brain cancer, kidney cancer, lymphoma, eye cancer, connective tissue cancer, Hodgkin's disease, bone cancer, testicular cancer, cervical cancer, thyroid cancer, melanoma, skin cancer, uterine cancer, lung cancer, colon cancer, rectal cancer, ovarian cancer, bladder cancer, larynx cancer, prostate cancer, stomach cancer, breast cancer, and pancreatic cancer. In preferred embodiments, the candidate subject has breast cancer cells. In particularly preferred embodiments, the candidate subject has metastatic breast cancer cells.

The present invention provides methods for identifying candidates for topoisomerase II inhibitor treatment, comprising: a) providing a candidate subject suspected of having breast cancer cells; b) detecting a copy number for both HER-2/neu and topoIIα in the breast cancer cells; and c) identifying the candidate subject as suitable for treatment with a topoisomerase II inhibitor, wherein the identifying comprises demonstrating amplification of the copy number for both HER-2/neu and topoIIα. In certain embodiments, the demonstrating comprises comparing the copy number of both HER-2/neu and topoIIα to a control copy number. In further embodiments, the copy number of HER-2/neu is at least 1.5 times greater than the control copy number. In additional embodiments, the copy number of topoIIα is at least 1.5 times greater than the control copy number. In further embodiments, the method further comprises step d) treating the candidate subject with a topoisomerase II inhibitor.

In some particularly preferred embodiments, the candidate subject is a human. In other embodiments, the candidate subject is a non-human animal. In some embodiments, the animal is a mammal (e.g., human, cat, dog, pig, or cow). In some preferred embodiments, the animal is a female, in other embodiments, the animal is a male. In some embodiments, the candidate subject has breast cancer cells (e.g., previously diagnosed as having breast cancer cells). In some preferred embodiments, the breast cancer cells are metastatic.

In some embodiments of the present invention, the detecting step comprises obtaining a tissue sample (e.g., biopsy) comprising the breast cancer cells from the candidate subject. In further embodiments, the detecting step further comprises contacting the tissue sample comprising the breast cancer cells with a first probe specific for the HER-2/neu and a second probe specific for the topoIIα. In certain embodiments, the second probe comprises at least about 100,000 nucleotides and hybridizes to a target region of human chromosome seventeen under in situ hybridization conditions, and wherein the target region contains topoIIα gene sequence, but does not contain HER-2/neu gene sequence.

In other embodiments, the first and second probes are detectably labeled nucleic acid. In further embodiments, the first probe is nucleic acid capable of hybridizing to HER-2/neu. In additional embodiments, the second probe is nucleic acid capable of hybridizing to topoIIα. In further embodiments, the first and second probes are detectably labelled. In particular embodiments, the detecting step comprises fluorescent in situ hybridization. In some embodiments, the detecting step comprises Southern blotting (hybridization) or Northern blotting (hybridization). In additional embodiments, the detecting step comprises Western blotting. In further embodiments, the detecting step comprises enzyme immunoassay (EIA). In certain embodiments, the detecting step comprises enzyme-linked immunosorbent assay (ELISA). In certain embodiments, the first and/or second probe is labelled with digoxigenin, and the first and/or second probe is fluorescently labelled. In other embodiments, the first and/or second probe is detected by chromogenic in situ hybridization. In certain embodiments, the first and/or second probe is detected by fluorescent in situ hybridization. In further embodiments, the detecting step comprises contacting the tissue sample comprising the breast cancer cells with an antibody specific for HER-2 (e.g., in order to detect a copy number for HER-2/neu) and a nucleic acid probe specific for topoIIα. In some particularly preferred embodiments, the detecting step comprises immunohistochemical detection and fluorescent in situ hybridization (FISH). However, it should be noted that any suitable method for detection of topoIIα and HER-2/neu finds use with the present invention.

The present invention further provides methods for identifying candidates for topoisomerase II inhibitor treatment, comprising: a) providing a candidate subject suspected of having breast cancer cells; b) detecting a copy number for both HER-2/neu and topoIIα in the breast cancer cells, wherein the detecting comprises contacting the breast cancer cells with a first probe specific for HER-2/neu, a second probe specific for topoIIα, and a control probe; and c) identifying the candidate subject as being suitable for treatment with a topoisomerase II inhibitor, wherein the identifying comprises demonstrating amplification of the copy number for both HER-2/neu and the topoIIα. In particular embodiments, the control probe is specific for human chromosome 17. In some particularly preferred embodiments, the topoisomerase II inhibitor is an anthracycline. In other embodiments, the anthracycline is selected from doxorubicin and epirubicin. In further embodiments, the breast cancer cells are metastatic.

The present invention provides methods for identifying candidates for topoisomerase II inhibitor treatment, comprising: a) providing a candidate subject comprising breast cancer cells, wherein the breast cancer cells comprise an amplified copy number for HER-2/neu, b) detecting a copy number topoIIα in the breast cancer cells; and c) identifying the candidate subject as suitable for treatment with a topoisomerase II inhibitor, wherein the identifying comprises demonstrating amplification of the copy number for topoIIα.

In particular embodiments, the demonstrating comprises comparing the copy number for topoIIα to a control copy number. In further embodiments, the copy number of the topoIIα is at least 1.5 times greater than the control copy number. In certain embodiments, the candidate subject is known to have an amplified copy number for HER-2/neu (e.g., previously determined by immunohistochemistry, FISH, chromogenic in situ hybridication, CISH, ELISA, etc.).

The present invention further provides methods comprising; a) providing a subject with cancer, wherein the subject comprises cancer cells with an amplified copy number of HER-2/neu and topoIIα, and b) treating the subject with a topoisomerase II inhibitor. In other embodiments, the candidate subject has been previously diagnosed as having cancer cells from diseases including, but not limited to, leukemia, brain cancer, kidney cancer, lymphoma, eye cancer, connective tissue cancer, Hodgkin's disease, bone cancer, testicular cancer, cervical cancer, thyroid cancer, melanoma, skin cancer, uterine cancer, lung cancer, colon cancer, rectal cancer, ovarian cancer, bladder cancer, larynx cancer, prostate cancer, stomach cancer, breast cancer, and pancreatic cancer. In preferred embodiments, the candidate subject has breast cancer cells. In particularly preferred embodiments, the candidate subject has metastatic breast cancer cells.

The present invention also provides methods comprising: a) providing a subject with breast cancer, wherein the subject comprises breast cancer cells with an amplified copy number of HER-2/neu and topoIIα, and b) treating the subject with a topoisomerase II inhibitor. In some embodiments, the topoisomerase II inhibitor is an anthracycline. In particular embodiments, the anthracycline is selected from doxorubicin and epirubicin. In further embodiments, the breast cancer cells are metastatic. In particularly preferred embodiments, the subject is a human. In other embodiments, the subject is a non-human animal. In still further embodiments, the animal is a mammal (e.g., human, cat, dog, pig, and cow). In preferred embodiments, the animal is a female, while in other embodiments, the animal is a male.

The present invention also provides compositions comprising a probe, the probe comprising at least about 100,000 nucleotides, wherein the probe hybridizes to a target region of human chromosome seventeen under in-situ hybridization conditions, and wherein the target region contains topoIIα gene sequence, but does not contain HER-2/neu gene sequence.

In certain embodiments, the probe comprises no more than 1 million nucleotides. In other embodiments, the probe comprises no more than 500,000 nucleotides, while in other embodiments, the probe comprises no more than 250,000 nucleotides. In further embodiments, the probe comprises about 140,00 to 200,000 nucleotides. In preferred embodiments, the probe comprises about 170,000 nucleotides. In particular embodiments, the probe comprises at least about 125,000, 140,000, 150,000, or 160,000 nucleotides. In some embodiments, the probe contains less than three percent repetitive nucleic acid sequences (e.g., ALU and LINE elements). In other embodiments, the probe contains less than two percent, or less than 1 percent repetitive nucleic acid sequences.

In particular embodiments, the probe further comprises a label. In certain embodiments, the label comprises digoxigenin. In other embodiments, the label is florescent. In particular embodiments, the label comprises biotin.

In certain embodiments, the target region is at least about 500,000 nucleotides from the HER-2/neu gene sequence (e.g. the site where the probe hybridizes on human chromosome 17 is at least 500,000 bases away from the HER2/neu gene). In other embodiments, the target region is at least about 400,000 or 300,000 or 200,000 nucleotides from the HER2/neu gene. In some preferred embodiments, the probe does not falsely detect HER2/neu instead of topoIIα. Also in some preferred embodiments, the target region target region comprises human chromosome locus 17q11–21.

In certain embodiments, the present invention provides kits and systems comprising the probe described above and at least one additional component. In some embodiments, the kits and systems of the present invention comprise; a) a composition comprising a probe, the probe comprising at least about 100,000 nucleotides, wherein the probe hybridizes to a target region of human chromosome seventeen under in-situ hybridization conditions, and wherein the target region contains topoIIα gene sequence, but does not contain HER-2/neu gene sequence, and b) at least one other component (e.g. insert component, primary antibody, secondary antibody, HER2 or HER2/neu probe, one or more buffers, digestion solution, cover slips, slides, graded alcohols, SSC buffer, etc). Example 9 provides additional components for inclusion in the kits of the present invention.

In some embodiments, the insert component comprises written material. In certain embodiments, the written material comprises instructions for using the probe (e.g. in an ISH procedure such as FISH or CISH). In other embodiments, the written material comprises instructions for testing patient breast cancer tissue samples to determine if a patient should be treated with a topoisomerase II inhibitor.

In certain embodiments, the probe further comprises a label (as detailed above). In some embodiments, the kits and systems of the present invention further comprise a first antibody specific for the label (e.g., FITC-anti-digoxigenin antibody). In particular embodiments, the kits and systems of the present invention further comprise a second antibody specific for the first antibody (e.g., HRP-anti-FITC antibody).

In other embodiments, the kits and systems of the present invention further comprise a second probe, wherein the second probe specifically detects HER2 or HER2/neu. In preferred embodiments, the second probe does not falsely detect topoIIα.

DESCRIPTION OF THE FIGURES

FIG. 2 shows the 3' end of the Exemplary topoIIα probe (SEQ ID NO:9), and the 5' end of the Exemplary topoIIα probe (SEQ ID NO:10).

DEFINITIONS

Figure 1:
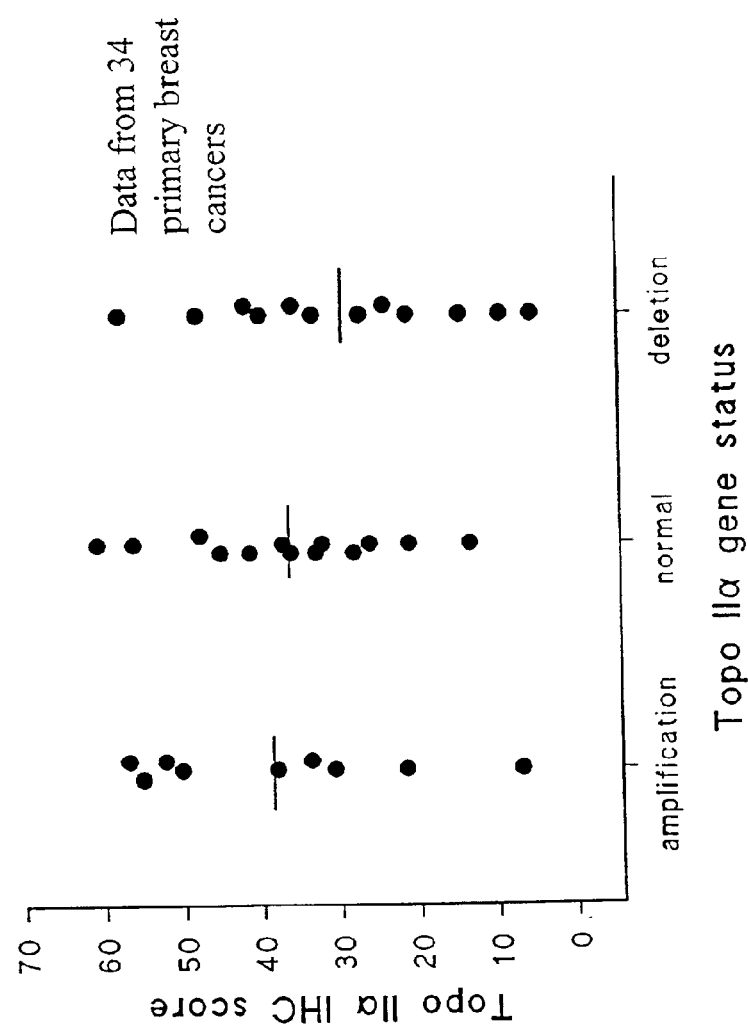
FIG. 1 shows the results of immunohistochemical and fluorescent in situ hybridization detection in 34 primary breast cancer samples.

To facilitate an understanding of the present invention, a number of terms and phrases are defined below:

As used herein, the term "candidate subject" refers to an animal (e.g., human) that is suspected of having cancer that may be evaluated for suitability for topoisomerase II inhibitor treatment. Examples of candidate subjects include, but are not limited to, human women suspected of having breast cancer and human men suspected of having breast cancer.

As used herein, the term "copy number" as used in reference to specific nucleic acid sequences (e.g., HER-2/neu, topoIIα, and control) refers to the actual number of these sequences per single cell. Copy number may be reported for one single cell, or reported as the average number in a group of cells (e.g., tissue sample). When comparing the "copy number" of cells (e.g., experimental and control cells) one need not determine the exact copy number of the cell, but instead need only obtain an approximation that allows one to determine whether a given cell contains more or less of the nucleic acid sequence as compared to another cell. Thus, any method capable of reliably directly or indirectly determining amounts of nucleic acid may be used as a measure of copy number even if the actual copy number is not determined.

As used herein, the term "HER-2/neu" refers to a nucleic acid sequence encoding the HER-2 protein, and includes both the wild-type sequence and naturally occurring variations, truncations, and mutations.

As used herein, the term "topoIIα" refers to a nucleic acid sequence encoding topoIIα protein, or portions thereof, and includes both the wild-type sequence and naturally occurring variations, truncations, and mutations.

As used herein, the term "suitable for treatment with topoisomerase II inhibitors" when used in reference to a candidate subject refers to subjects who are more likely to benefit from treatment with topoisomersase II inhibitors than a subject selected randomly from the population. For example, using the screening methods of the present invention as described in Example 6, 79% of the subjects selected responded to topoisomerase II inhibitor treatment (as compared to 10% or less if subjects were randomly selected from the population, or as compared to approximately 30–40% of metastatic breast cancer patients).

As used herein, the term "amplification" when used in reference to copy number refers to the condition in which the copy number of a nucleic acid sequence (e.g., HER-2/neu) is greater than the copy number of a control sequence (e.g., chromosome 17). In other words, amplification indicates that the ratio of a particular nucleic acid sequence (e.g., HER-2/neu) is greater than 1:1 when compared to a control sequence (e.g., 1.1:1, 1.2:1, or 1.3:1). In preferred embodiments, the ratio of a particular nucleic acid sequence is at least 1.5 times greater than the control sequence copy number (i.e., 1.5:1).

As used herein, the term "nucleic acid molecule" and "nucleic acid sequence" refer to any nucleic acid containing molecule including, but not limited to DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "hybridization" is used in reference to the pairing of complementary nucleic acids.

Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "probe" refers to an oligonucleotide (i.e., a sequence of nucleotides), whether occurring naturally as in a purified restriction digest or produced synthetically, recombinantly or by amplification (e.g. PCR), which is capable of hybridizing to another oligonucleotide of interest. Probes useful in the present invention may be single-stranded or double-stranded. Probes are useful in the detection, identification and isolation of particular gene sequences (e.g., HER-2/neu, topoIIα, and chromosome 17). It is contemplated that any probe used in the present invention may be labelled with any "reporter molecule," so that is detectable in any detection system, including, but not limited to enzyme (e.g., ELISA, as well as enzyme-based immunohistochemical assays), fluorescent (e.g., FISH), radioactive, mass spectroscopy, and luminescent systems. It is not intended that the present invention be limited to any particular detection system or label.

As used herein, the term "label" refers to any molecule which may be detected. For example, labels include, but are not limited to, $^{32}P$, $^{14}C$, $^{125}I$, $^{3}H$, $^{35}S$, biotin, digoxigenin, avidin, fluorescent or enzymatic molecules.

As used herein, the phrase "repetitive nucleic acid sequences" refers to nucleic acid sequence within a genome which encompass a series of nucleotides which are repeated many times, often in tandem arrays. The repetitive sequences can occur in the genome in multiple copies ranging from two to hundreds of thousands of copies and may be clustered or interspersed on one or more chromosomes throughout a genome. Although repetitive nucleic acid sequences may be present throughout the genome, a large number of the repetitive nucleic acid sequences are typically located at the centromere of each chromosome. Examples of repetitive nucleic acid sequences include, but are not limited to, ALU and LINE elements.

As used herein, the terms "in situ hybridization" and "ISH" refer to methods for detecting and localizing nucleic acids within a cell or tissue preparation. These methods provide both quantitative and spacial information concerning the nucleic acid sequences within an individual cell or chromosome. ISH has been commonly used in many areas, including prenatal genetic disorder diagnosis, molecular cytogenetics, to detect gene expression and overexpression, to identify sites of gene expression, to map genes, to localize target genes and to identify various viral and microbial infections, tumor diagnosis, in vitro fertilization analysis, analysis of bone marrow transplantation and chromosome analysis. The technique generally involves the use of labeled nucleic acid probes which are hybridized to a chromosome or mRNA in cells that are mounted on a surface (e.g slides or other material). The probes can be labelled with fluorescent molecules or other labels. One example of fluorescent in situ hybridization (FISH) is provided in Kuo et al., *Am. J. Hum. Genet.*, 49:112–119, 1991 (hereby incorporated by reference). Other ISH and FISH detection methods are provided in U.S. Pat. No. 5,750,340 to Kim et al., hereby incorporated by reference. Further examples of fluorescent in situ hybridization, as well as chromogenic in situ hybridization are provided in Examples 1–10 below. Additional protocols are known to those of skill in the art.

As used herein, the phrase "under in situ hybridization conditions" refers to any set of conditions used for performing in situ hybridization (ISH) that allows the successful detection of labelled oligonucleotide probes. Generally, the conditions used for in situ hybridization involve the fixation of tissue or other biological sample onto a surface, prehybridization treatment to increase the accessibility of target nucleic acid sequences in the sample (and to reduce non-specific binding), hybridization of the labelled nucleic acid probes to the target nucleic acid, post-hybridization washes to remove unbound probe, and detection of the hybridized probes. Each of these steps is well known in the art and has been performed under many different experimental conditions. Again, examples of such in situ hybridization conditions are provided in Kuo et al., U.S. Pat. No. 5,750,340, and Examples 1–10 (below). Further examples of conditions and reagents useful for performing in situ hybridization are provided below.

The tissue or biological sample can be fixed to a surface using fixatives. Preferred fixatives cause fixation of the cellular constituents through a precipitating action which is reversible, maintains a cellular morphology with the nucleic acid in the appropriate cellular location, and does not interfere with nucleic acid hybridization. Examples of fixatives include, but are not limited to, formaldehyde, alcohols, salt solutions, mercuric chloride, sodium chloride, sodium sulfate, potassium dichromate, potassium phosphate, ammonium bromide, calcium chloride, sodium acetate, lithium chloride, cesium acetate, calcium or magnesium acetate, potassium nitrate, potassium dichromate, sodium chromate, potassium iodide, sodium iodate, sodium thiosulfate, picric acid, acetic acid, sodium hydroxide, acetones, chloroform glycerin, and thymol.

After being fixed on a surface, the samples are treated to remove proteins and other cellular material which may cause nonspecific background binding. Agents which remove protein include, but are not limited to, enzymes such as pronase and proteinase K, or mild acids, such as 0.02.–0.2 HCl, as well as RNase (to remove RNA).

DNA on the surface may then denatured so that the oligonucleotide probes can bind to give a signal. Denaturation can be accomplished, for example, by varying the pH, increasing temperature, or with organic solvents such as formamide. The labeled probe may then hybridize with the denatured DNA under standard hybridization conditions. The tissue or biological sample may be deposited on a solid surface using standard techniques such as sectioning of tissues or smearing or cytocentrifugation of single cell suspensions. Examples of solid surfaces include, but are not limited to, glass, nitrocellulose, adhesive tape, nylon, or GENE SCREEN PLUS.

DESCRIPTION OF THE INVENTION

The present invention relates to methods for diagnosing and treating cancer, and in particular, methods for determining the susceptibility of subjects suspected of having breast cancer (or known to have breast cancer) to treatment with topoisomerase II inhibitors. The present invention also relates to in situ hybridization probes for specifically detecting topoIIα gene sequences.

In some embodiments, the present invention provides methods for determining whether a subject suspected of having breast cancer would benefit from treatment with topoisomerase II inhibitors (e.g., anthracyclines). For example, the present invention provides diagnostic assays for detecting an amplified copy number of HER-2/neu and topoIIα in breast cancer cells of a candidate subject, and identifying whether the candidate subject is suitable for treatment with topoisomerase II inhibitors. In other embodiments, the present invention provides methods for treating breast cancer by administering topoisomerase II inhibitors (e.g., anthracyclines) to subjects, with breast cancer cells with an amplified copy number of HER-2/neu and topoIIα. For ease in reading, the Description of the Invention is divided into the following sections: I. Breast Cancer; II. Treatment for Metastatic Breast Cancer; III. TopoIIα and topoIIα, IV. Detection of TopoIIα, V. HER-2 and HER-2/neu; VI. Detection of HER-2 and HER-2/neu; VII.; HER-2/neu—TopoIIα Relationship; and VIII. HER-2/neu—TopoIIα Status as Diagnostic Marker.

I. Breast Cancer

Despite earlier diagnosis of breast cancer, about 1–5% of women with newly diagnosed breast cancer have a distant metastasis at the time of the diagnosis. In addition, approximately 50% of the patients with local disease who are primarily diagnosed eventually relapse with the metastasis. Eighty-five percent of these recurrences take place within the first five years after the primary manifestation of the disease.

On presentation, most patients with metastatic breast cancer have only one or two organ systems involved. As the disease progresses over time, multiple sites usually become involved. Indeed, metastases may be found in nearly every organ of the body at autopsy. The most common sites of metastatic involvement observed are locoregional recurrences in the skin and soft tissues of the chest wall, as well as in axilla, and supraclavicular area. The most common site for distant metastasis is the bone (30–40% of distant metastasis), followed by lung and liver. Metastatic breast cancer is generally considered to be an incurable disease. However, the currently available treatment options often prolong the disease-free state and overall survival rate, as well as increase the quality of the life. The median survival from the manifestation of distant metastases is about three years.

In some patients, advanced disease can be controlled with therapy for many years allowing good quality of life. This is particularly evident for those patients with hormone receptor positive disease and nonvisceral sites of metastases. It is contemplated that with better understanding of the molecular factors involved in the response to chemotherapy and increased efficiency of chemotherapy, regimens will substantially extend the survival for these patients, and in some patients, perhaps even extend survival to their otherwise natural life-span. However, despite these promises, the current reality is that treatment provides only temporary control of cancer growth for most patients with metastatic breast cancer.

II. Treatment for Metastatic Breast Cancer

Systemic drug therapy for advanced breast cancer is usually started with hormonal therapy due to its lower toxicity than the cytotoxic chemotherapies. The best candidates for hormonal therapy, based on their clinical features, are patients with a hormone receptor positive tumor (especially when both hormone receptors are positive), long term disease free survival, previous response to hormonal therapy, and non-visceral disease. Despite short second-line and even third-line responses to alternative hormonal therapies (e.g., second anti-estrogen or aromatase inhibitor) in advanced stage of breast cancer, nearly all patients finally become refractory to hormonal therapy and their disease progresses.

Due to its higher toxicity, cytotoxic chemotherapy is given to patients with disease refractory to hormonal therapy. In addition, it is frequently used as the first-line therapy for those with extensive visceral involvement of metastatic disease (e.g., lung or liver metastasis), with hormone receptor negative primary tumor, with extensive involvement of bone marrow, or with tumor that is so rapidly growing that the response to hormonal therapy can not be monitored. Combination chemotherapy for advanced breast cancer is generally considered more efficacious than single-agent therapy. However, randomized trials have shown that similar response rates can be achieved with single-agent therapy.

Advanced breast cancer is currently considered to be incurable and nearly all available chemotherapeutic drugs have been tested for use in its treatment. Among the large number of cytotoxic drugs, anthracyclines (which are topoII-inhibitors), especially doxorubicin and its derivative epirubicin, and taxanes are considered to be the most efficacious. The optimal schedules for the newer drugs, paclitaxel and docetaxel (taxanes), are yet to be established.

In addition to anthracyclines, other topoIIα-inhibitors include cytotoxic agents such as etoposide, amsacrine, and mitoxantrone. All these agents target the topoisomerase IIα enzyme (topoIIα) and are now routinely employed in the systemic treatment of hematological cancers and solid tumors. Generally, the chemotherapeutic regimens for the most curable malignancies, such as lymphomas and leukemias, as well as for breast cancer are based on such agents that act on topoIIα.

In the treatment of breast cancer, these compounds are not only given for patients with metastatic disease, but are also gaining popularity as a foundation for adjuvant chemotherapy regimens. Whether given alone or combined with other cytotoxic drugs, the objective response rate to anthracyclines generally ranges from 40% to 80% in metastatic breast cancer. However, the rate of complete response is approximately 5–15% and usually lasts for one to two years in these patients. The proportion of patients who achieve complete, prolonged (i.e., several years) remissions is below 1%. More typically, the response is partial (50% reduction in tumor mass) and its duration ranges from 6 to 12 months. Thus, there is still a large number of patients who do not receive objective, clinical response to these cytotoxic drugs. In these patients the disease progression may just be halted or continue to progress despite the treatment. About 40–60% of the breast cancer patients receiving anthracyclines have either stabilized or develop progressive disease during the therapy. Therefore, there is a need for reliable selection of patients who are likely to respond to therapy from those likely to have primary resistance to anthracyclines.

As important as it is to identify the patients likely to respond to therapy, it may be even more relevant to identify patients who are not likely to achieve any objective response to anthracyclines, because the tumors resistant to anthracyclines also acquire resistance to other classes of cytotoxic drugs during anthracycline therapy (i.e., the tumors become multi-drug resistant (MDR)). The MDR phenotype turns cancer cells resistant to virtually any form of cytotoxic chemotherapy (excluding the taxanes). Indeed, MDR tumor cells are even resistant to agents with no functional or mechanistic interaction with topoII-inhibitors.

The most recent breakthrough in the treatment of human malignancies has been the introduction of monoclonal antibodies which specifically target genes that are involved in the pathogenesis of cancer. The first such antibody targeting human oncogene is called Trastuzumab (HERCEPTIN, Genentech BioOncology, Roche), and was introduced to the treatment of breast cancer patients in 1997. HERCEPTIN specifically binds the extracellular domain of the HER-2 and abolishes growth factor signalling through HER-2 and other growth factor receptors attached to HER-2.

In clinical trials, HERCEPTIN was shown to be generally well tolerated with the most common adverse effects being chills and fever in approximately 40% of patients (mainly associated with the first infusion). However, when administered in conjunction with anthracyclines, HERCEPTIN resulted in an increased risk of cardiac dysfunction in patients. In particular, it has been reported that 27% of patients receiving combined therapy with HERCEPTIN and anthracyclines experienced cardiac dysfunction, while only 6% of patients receiving anthracycline therapy alone experienced cardiac dysfunction. Thus, the present invention provides methods for identifying candidate subjects that would benefit from anthracycline therapy, even though they may initially be viewed as HERCEPTIN therapy candidates.

III. TopoIIα and TopoIIα

Topoisomerases are enzymes involved in resolving topological problems that arise during the various processes of DNA metabolism, including transcription, recombination, replication, and chromosome segregation during cell division. As a result of performing these vital functions, topoisomerases are necessary for the viability of all living organisms.

Topoisomerases are classified into "Type I" and "Type II" based on their catalytic activity. Type I enzymes introduce transient single-stranded breaks into DNA, pass a single intact strand of DNA through the broken strand, and re-ligate the break. Type II enzymes, in contrast, make transient double-stranded breaks in one segment of replicated DNA and pass an intact duplex through the broken double-stranded DNA.

Among different topoisomerase enzymes, type II DNA topoisomerases (topoII) are essential in the segregation of newly replicated chromosome pairs, chromosome condensation, forming chromosome scaffolds, and altering DNA superhelicity. The reaction of transporting the intertwined double-stranded DNA through a double-stranded break favors a "two-gate model". In this model, topoII forms an ATP-operated clamp through which the first segment of DNA binds and which then captures the DNA segment to be transported. Once the transported segment has passed through the break in the bound DNA, it is allowed to leave the enzyme by another gate on the other side of the molecule, while the double-stranded break in the bound DNA is simultaneously re-sealed by the enzyme. Consistent with this biochemical model of the enzyme as an ATP-modulated clamp with two sets of jaws at opposite ends, connected by multiple joint, the crystal structure of topoII reveals a heart-shaped dimeric protein with a large central hole.

The eukaryotic topoII is a homodimeric enzyme that exists in two isoforms in human cells, the major, 170-kd topoIIα and 180-kd topoIIβ. These two enzymes share considerable homology (72%) but are products of different genes located in chromosomes 17q21–q22 and 3p, respectively. The functions as well as the expression of these two genes are different. Whereas topoIIα expression is cell cycle-dependent, the β-isoform shows no cell cycle-phase dependency. The most abundant expression of topoIIα takes place at the G2/M-phase of the cell cycle and declines to minimum at the end of mitosis. The exact function of topoIIβ is still largely unknown.

TopoIIα has raised considerable clinical interest since it is a molecular target for many antineoplastic and antimicrobial drugs. Among the cytotoxic drugs acting on inhibiting topoIIα are some of the most important anticancer drugs such as anthracyclines (e.g., doxorubicin, epirubicin, daunorubicin, idarubicin), epipodophyllotoxins (e.g., etoposide, teniposide), actinomycin and mitoxantrone. Although these anticancer drugs share no structural homology, they all act by trapping topoIIα in a covalently bound reversible complex with DNA, termed the 'cleavable complex'. The stabilization of cleavable complexes prevents the religation of the double-stranded breaks. This converts topoIIα into a physiological toxin and introduces high levels of permanent double-stranded breaks that are ultimately detected by cell cycle checkpoint and culminate in cell death by apoptosis.

It has been shown in vitro that sensitivity to topoII-inhibitors correlates with the expression level of topoIIα in cancer cells. Cells with low nuclear concentrations of topoIIα protein form fewer topoII-mediated DNA strand breaks and are thus less sensitive to topoII-directed drugs than cells containing high amounts of topoIIα. This relationship was first established by comparing the chemosensitivity of different cell lines to their expression of topoIIα, but more recently the relationship has been confirmed with more specific methods. These studies have shown that sensitive cell lines can be made resistant by transfection of either antisense topoIIα mRNA or mutant topoIIα cDNA. The transfection of exogenous, wild-type topoIIα mRNA, in turn, reverses primary resistance to topoII-inhibitors into sensitivity.

IV. Detection of TopoIIα

Detection of the amplification of the topoisomerase IIa (topoIIα) gene may be determined, for example, by employing in situ hybridization (e.g., FISH or CISH, See, Examples below). Probes for topoIIα may be obtained, for example, by screening a P1-library, and confirming the identity of the probe by performing PCR with topoIIα specific primers (See, Example 1). BAC or PAC clones may also be used for TopoIIα probe preparation. In preferred embodiments, a TopoIIα probe that is capable of specifically detecting TopoIIα gene sequence (without falsely detecting HER2/neu) are employed. It should be noted that the TopoIIα probes briefly sold by Vysis (Downers Grove, Ill.), were unable to accurately discriminate between TopoIIα and HER2/neu. However, the present invention provides such specific probes (e.g., the Exemplary probe described in Example 8, and commercially available from Zymed Laboratories).

V. HER-2 and HER-2/neu

The HER-2/neu oncogene (also known as erbB-2) encodes a 185-kDa transmembrane glycoprotein (HER-2), which is a member of the family of epidermal growth factor (EGF) receptor tyrosine kinases (RTK). The HER-2 family of RTKs has four members: HER-1, HER-2, HER-3, and HER-4. The RTKs are cell-surface enzymes consisting of a single transmembrane domain separating an intracellular kinase domain from an extracellular ligand-binding domain. Ligand binding to the extracellular domain induces the formation of receptor dimers (homo- or preferentially hetero-), which are essential for activation of the intrinsic tyrosine kinase activity. This subsequently leads to a recruitment of target proteins, that initiate a complex signalling cascade.

Although a large number of putative candidate ligands (EGF, heparin binding EGF-like growth factor, transforming growth factor-α, amphiregulin, betacellulin, epiregulin and a large family of different neuregulins among others) have been postulated to bind HER-2, none of these peptides binds HER-2 with high affinity. However, EGF-like ligands are bivalent. Thus, they are capable of binding their receptors at two different sites; namely high affinity as well as low affinity binding sites. Although HER-2 is not a high affinity receptor for any of the ligands shown to bind ErbBs, it is the preferred low affinity co-receptor for EGF-like ligands. Therefore, it emerges as the preferred dimer-mate for the three other ErbBs, once these primary receptors are occupied by their ligands. Thus, at least 20 growth factors can utilize HER-2 related signalling pathways.

HER-2 is vital in the induction of growth signal by the ligand occupied ErbBs, because in the presence of HER-2:1) it is the preferred heterodimerization partner for all ligand-binding ErbB RTKs and 2) HER-2-containing heterodimers are also characterized by extremely high growth factor-induced signalling potency and mitogenesis. The high signalling potency of HER-2 containing heterodimers, in turn, is attributed to several specific features: 1) HER-2 reduces the rate of ligand dissociation from its high affinity receptor; 2) HER-2 induces lateral signalling by recruiting and activating other (unoccupied) ErbB receptors; and 3) HER-2 efficiently signals through protein kinases (such as MAP and Jun N-terminal), which are especially potent activators of mitosis. In addition, HER-2-containing receptor dimers are recycled from endosomes back to the cell surface instead of being degraded by lysosomes. Thus, these dimers may be overrepresented at the cell surface.

Due to these features, the HER-2 receptor has an oncogenic potential that may be activated through multiple genetic mechanisms including point mutations, truncation of the protein, and the amplification of the non-mutated proto-oncogene. However, gene amplification is by far the most common mechanism for the activation of the oncogenic potential of HER-2. The amplification of HER-2/neu happens in approximately 20 to 35% of invasive breast cancers and results in overexpression of the protein. Thus, the amplification of HER-2/neu increases the likelihood of HER-2 to form heterodimeric complexes with the other ErbBs. This, in turn, indicates that several dozen potentful ligands can take advantage of HER-2 dependent signalling pathways leading to the oncogenic activation of cells.

The association of HER-2/neu and the prognosis for breast cancer patients has been extensively studied (e.g., Ravdin and Chamness, Gene, 159:19–27, [1995]). Unfortunately, amplification of HER-2/neu has been found to be associated with poor clinical outcome. However, whether HER-2/neu is an independent prognostic factor is still controversial because both supportive and non-supportive results have been published (e.g., Ravdin and Chamness, supra).

The most common activation mechanism for HER-2/neu is by the amplification of the gene at 17q12–q21. The extra copies of HER-2/neu oncogene are deposited in cancer cells as extrachromosomal double minute chromosomes or within the chromosomes in homogeneously staining regions.

The predictive value of HER-2/neu has also been studied, although not as extensively as its prognostic value, in conjunction with both adjuvant chemotherapy and in chemotherapy for advanced breast cancer (e.g., McNeil, C., J. Natl. Cancer Inst., 91:100, [1999]). HER-2/neu appears to be a predictor for poor clinical outcome in adjuvant chemotherapy by conventional cyclophosphamide-methotrexate-fluorouracil-combination. The relationship of amplified HER-2/neu and topoII-inhibitor chemotherapy in breast cancer is more controversial. Most studies have linked amplified HER-2/neu to chemoresistance to topoII-inhibitors (See, e.g., Tetu et al., Mod. Pathol., 11:823 [1998]), but there are also clinical trials reporting either no association (See, e.g., Clahsen et al., J. Clin. Oncol., 16:470 [1998]), or even tendency for higher response rates among HER-2/neu-amplified breast tumors (See, e.g., Thor et al., J. Natl. Cancer Inst., 90:1346 [1998]). The results presented in Example 5 below support the conclusion that HER-2/neu amplification is not associated with clinical response to topoisomerase II inhibitors.

VI. Detection of HER-2 and HER-2/neu

As noted above, HER-2/neu oncogene amplification and its concomitant protein overexpression are currently implicated as an important prognostic biomarker in breast carcinoma, and may also be a useful determinant of response to hormonal or cytotoxic chemotherapy. The clinical importance of HER-2/neu diagnostics has become even more significant with the increasing use of the new anti-cancer drug trastuzumab (HERCEPTIN, a humanized monoclonal antibody against the extracellular part of the HER-2/neu protein product). However, trastuzumab therapy is effective only in patients whose tumors contain amplification and/or overexpression of HER-2 (Shak. S., Semin. Oncol., 6:71 [1999]). Thus, HER-2 assays are now becoming an important part of breast cancer diagnostics, in parallel with assays of hormone receptors and tumor proliferation rate.

The earliest studies of HER-2 used Southern and Western blotting for detection of HER-2/neu gene amplification and HER-2 protein overexpression. However, these methods are not well-suited for routine diagnostics and have been replaced by immunohistochemistry and fluorescence in situ hybridization (FISH). In addition, a vast majority of HER-2 studies have been done using immunohistochemistry (IHC), which detects the HER-2 protein overexpression on the cell membrane. Without HER-2/neu oncogene amplification, the protein expression is generally low and undetectable by IHC. However, IHC is subject to a number of technical artifacts and sensitivity differences between different antibodies and tissue pretreatments. Standardized reagent kits have recently been introduced (e.g., HERCEP-TEST, Genentech), but mixed results have been reported from their methodological comparisons (Jiminez et al., Mod. Pathol., 13:37 [2000]). Other HER-2 commercially available antibodies include two monoclonal antibodies from Novocastra Laboratories, clone CB-11 and NCLB12.

Fluorescent in situ hybridization (FISH) quantifies the number of gene copies in the cancer cell nucleus. Since the initial experiments to detect HER-2/neu amplification by FISH, a number of reports have verified its accuracy both in freshly frozen and paraffin-embedded tumor material (Mitchell, M. S., Semin. Oncol., 26:108 [1999]). FISH is generally performed using either single-color (HER-2/neu probe only) or dual-color hybridization (using HER-2/neu and control probes (e.g., chromosome 17 centromere probes simultaneously), with the latter method making it easier to distinguish true HER-2/neu amplification from chromosomal aneuploidy. FISH using entire cells (e.g., cultured cells, pulverized tissue, or imprint touch specimens from tumors) is considered straightforward, but the use of tissue sections complicates the quantitative nature of FISH due to nuclear truncation (i.e., due to the slicing of the tissues during their preparation for staining). Commercially available FISH probes include Zymed's SPoT-LIGHT HER-2/neu probe (Zymed Laboratories, San Francisco, Calif.), and Vysis's LSI HER-2/neu SpectrumOrange probe (Vysis, Downer's Grove, Ill.).

The main difficulty in adopting FISH for clinical diagnostic use is the requirement for fluorescence microscopy. Evaluation of FISH samples generally requires a modern epifluorescence microscope equipped with high-quality 60× and 100× oil immersion objectives and multi-bandpass fluorescence filters. Moreover, because the fluorescence signals fade within a few weeks, the hybridization results usually must be recorded with expensive CCD cameras.

One aspect of the present invention circumvents many of these problems by providing methods and compositions for detecting HER-2/neu that are rapid and do not require the use of fluorescence microscopy. In particular, the present invention provides Chromogenic In Situ Hybridization (CISH) HER-2/neu detection probes and methods (See, Example 7) that allow enzymatic detection of HER-2/neu. As described in Example 7, the present invention provides a HER-2/neu probe capable of detection by bright field microscopy. Such probes and detection reagents are commercially available from Zymed Inc. (South San Francisco, Calif.). Another advantage of the HER-2/neu probe is the ability to perform CISH and histopathology simultaneously on the same tissue sample (See, Example 7).

VII. HER-2/neu—TopoIIα Relationship

The relationship between HER-2/neu and topoIIα amplification has been previously studied. Indeed, topoIIα has been found to be amplified in breast tumors with HER-2/neu amplification [e.g., Smith et al., *Oncogene*, 8:933 (1993)]. As TopoIIα and HER-2/neu are located so close to each other on chromosome 17, that a simple molecular mechanism for this phenomenon previously hypothesized involves amplification of the chromosomal segment bearing both genes [Murphy et al., *Int. J. Cancer*, 64:18–26 (1996), Hoare et al., *Br. J. Cancer*, 75:275 (1997)]. This should lead to similar gene copy numbers for HER-2/neu and topoIIα. However, during the development of the present invention, as detailed in Example 3, imbalanced copy numbers for HER-2/neu and topoIIα were found by employing fiber FISH analysis. As discussed in Example 3, the presence of two separate amplicons for closely situated genes such as HER-2/neu and topIIα was unexpected.

The relationship between HER-2/neu and topoIIα amplification and the response of breast cancer cell lines to topoisomerase inhibitors has also been previously been studied. For example, one group reported that a breast cancer cell line with amplification of both HER-2/neu and topoIIα was the most sensitive to m-AMSA and mitoxantrone. [Smith et al., supra]. Subsequent to the breast cancer cell line work, the effect of topoisomerase inhibitors on primary breast cancer cells was evaluated in primary breast cancer cells determined to have amplified HER-2/neu and topoIIα [Jarvinen, et al., *British Journal of Cancer*, 77(12):2267 (1998)]. However, instead of confirming the results previously reported for breast cancer cell lines, the primary breast cancer cells with amplification of both HER-2/neu and topoIIα were not found to exhibit a positive response to topoisomerase inhibitors. Thus, the art would predict that the present invention would not work. Nonetheless, the surprising results obtained during the development of the present invention indicates that the methods described herein do work. In this regard, the results presented in the Examples below were unexpected.

VIII. HER-2/neu—TopoIIα Status as Diagnostic Marker

The present invention provides diagnostic markers for cancer (e.g., breast cancer). In particular, the present invention provide methods for determining whether a candidate subject is suitable for topoisomerase II inhibitor treatment by detecting copy number amplification of both HER-2/neu and topoIIα. In some embodiments, the present invention provides methods for identifying a candidate for topoisomerase II inhibitor treatment by providing a candidate subject suspected of having breast cancer cells and detecting a copy number for both HER-2/neu and topoIIα in the breast cancer cells. In this regard, the method allows identification of the candidate subject as suitable for treatment with a topoisomerase II inhibitor by demonstrating amplification of the copy number for both the HER-2/neu and the topoIIα. In some embodiments, the candidate subject has breast cancer cells comprising an amplified copy number for HER-2/neu. (e.g., HER-2/neu amplification was already determined).

In certain embodiments, the detecting is performed with HER-2/neu and topoIIα specific probes (e.g., fluorescent in situ hybridization). While not limiting the present invention to any particular mechanism, and not necessary to the successful practice of the present invention, it is believed that detecting the nucleic acid of topoIIα instead of the expressed protein product (e.g., by immunohistochemistry) allows amplification of both HER-2/neu and topoIIα to serve as a diagnostic marker for breast cancer cells susceptible to treatment with topoisomerase II inhibitors. In particular, as demonstrated in Example 4, there is a lack of correlation between topoIIα gene status and immunohistochemical (IHC) detection. Consequently, assessment of topoIIα gene expression using IHC detection fails to yield a relationship between amplification of both topoIIα and HER-2/neu in regard to predicting the response of primary breast cancer cells to topoisomerase II inhibitors. Thus, the present invention provides a breast cancer marker for response to anthracycline based therapy by detecting copy number for both HER-2/neu (e.g., employing IHC or nucleic acid probes) and topoIIα (e.g., employing nucleic acid probes). As such, the present invention provides improved methods for identifying breast cancer patients suitable for treatment with topoisomerase II inhibitors, as well as patients that should not receive topoisomerase II inhibitors (e.g., anthracycline).

Importantly, the present invention allows assessment of patients found to have HER-2/neu amplification (i.e., an indicator for HERCEPTIN treatment). Indeed, testing to determine whether anthracycline treatment is appropriate (amplification of both HER-2/neu and topoIIα) or if HERCEPTIN treatment is appropriate (only HER-2/neu amplification). This capability is of particular importance in view of the human trials that have identified serious risks associated with co-administering both anthracyclines and HERCEPTIN.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); Sigma (Sigma Chemical Co., St. Louis, Mo.).

Example 1

TopoIIα and HER-2/neu Gene Copy Numbers In Breast Cancer Cell Lines

This examples describes the characterization of topoIIα and HER-2/neu gene copy numbers in nine breast cancer cell lines by dual color fluorescent in situ hybridization (FISH) assays. The nine breast cancer cell lines assayed were: BT-474, DU4475, MCF-7, MDA-157, MDA-361, SK-BR-3, ZR-75-1, UACC-812, and UACC-893. A normal human lymphocyte cell line was also used. All cell lines were obtained from the American Type Culture Collection (ATCC, Rockville, Md.). The breast cancer cell lines were grown using recommended culture conditions and harvested at confluency to obtain interphase nuclei from cells that were predominantly in the G1-phase of the cell cycle. The cells were subsequently fixed in methanol:acetic acid (3:1) and placed on microscope slides (see, Tanner et al., Cancer Res., 54:4257 [1994]).

Dual-color FISH experiments were done as known in the art (See e.g., Tanner et al., supra), employing probes for HER-2/neu, topoIIα, and chromosome 17. The HER-2/neu probe employed was P1 clone (RMC17P077) obtained from the Resource for Molecular Genetics (Berkeley, Calif.). A P1 probe for topoIIα was obtained by screening a P1-library (Genome Systems Inc., St. Louis, Mo.). The specificity of the HER-2/neu and topoIIα probes was confirmed by PCR with primers amplifying fragments of HER-2/neu, topoIIα, retinoic acid receptor alpha, and thyroid receptor alpha 1. The following primer sequences were used for topoIIα, 5'-GCCTCCCTAACCTGATTGGTTT-3' (SEQ ID NO:1), and 5'-CTGAAGAACCCTGAAAGCGACT-3' (SEQ ID NO:2), resulting in the generation of a 259 base pair PCR product. For HER-2/neu, the following primers were used, 5'-CTGGCTCCGATGTATTTGATG-3' (SEQ ID NO:3), and 5'-CCTGCCCATAAGTCTCTCTGCT-3' (SEQ ID NO:4), resulting in the generation of a 210 base pair PCR product. For retinoic acid receptor alpha, the following primers were used, 5'-GATTAGCCTGCCCTCTTTGG-3' (SEQ ID NO:5) and 5'-CAGAAGGGAGGCAGACAGTC-3' (SEQ ID NO:6), resulting in the generation of a 148 base pair PCR product. For thyroid hormone receptor alpha 1, the following primers were used, 5'-GCTCATGGTGTC-AGGAGGATG-3' (SEQ ID NO:7), and 5'-GCAGGAATAGGTGGGATGGAG-3' (SEQ ID NO:8), resulting in the generation of a 196 base pair PCR product. The PCR conditions were optimized for each primer pair for corresponding gene using PTC-100 thermocycler (MJ Research Inc, Watertown, Mass., USA). Approximately 100 ng of each template probe and 25 pmol of corresponding primers were used in a 25 μl reaction volume in a standard reaction mixture recommended for use with DYNAZYME II thermostable DNA polymerase (Finnzymes Oy, Espoo, Finland).

A chromosome 17 pericentromeric probe (p17H8) was used to determine the copy number of chromosome 17. A gene/locus specific probe (HER-2/neu or topoIIα) was hybridized together with the 17 centromere probe. The probes were labelled with biotin-14-dATP and digoxigenin-11-dUTP. The HER-2/neu and topoIIα probes were also hybridized together (one labelled with biotin, another with digoxigenin). After hybridization, the bound probes were detected with avidin-FITC (for the biotin-labelled probe) and anti-digoxigenin rhodamine. Slides were counterstained with 0.2 mm 4,6-diamidino-2-phenylindole (DAPI) in an antifade solution (Vectashield, Vector Laboratories, Burlingame, Calif.).

Hybridization signals were evaluated using an Olympus BX50 epifluorescence microscope equipped with a 63× oil-immersion objective (numeric aperture 1.4). A dual band-pass fluorescence filter (Chromotechnology; Brattleboro, Vt.) was used to separately and simultaneously visualize the FITC and rhodamine signals. Approximately 50 non-overlapping nuclei with intact morphology based on DAPI counterstaining were scored to determine the number of hybridization signals for each of the three probes (i.e., topoIIα, HER-2/neu, and 17 centromere probes). Control hybridizations to normal lymphocyte interphase nuclei were done to ascertain that the probes recognized a single-copy target and that the hybridization efficiencies of the probes used were similar. In these experiments, amplification of HER-2/neu and topoIIα were indicated, if the average ratio of HER-2/neu or topoIIα signals, relative to chromosome 17 centromere signals was 1.5 or more. TopoIIα was considered deleted, in this example, if the ratio was <0.7. The results of this dual color FISH assay are presented in Table 1.

TABLE 1

Absolute and Relative Numbers of topoIIα and HER-2/neu in Breast Cell Lines

| Cell Line | HER-2/neu copy number Absolute (mean ± SD) | HER-2/neu copy number Relative to 17 centromere | TopoIIα copy number Absolute (mean ± SD) | TopoIIα copy number Relative to 17 centromere |
|---|---|---|---|---|
| Lymphocytes | 2.0 ± 0.4 | 1.0 | 2.1 ± 0.4 | 1.1 |
| BT-474 | 53 ± 6.2 | 8.0* | 4.2 ± 0.6 | 1.0 |
| DU-4475 | 4.3 ± 0.9 | 1.1 | 4.0 ± 0.4 | 1.0 |
| MCF-7 | 2.7 ± 0.8 | 0.7 | 3.9 ± 0.9 | 1.0 |
| MDA-157 | 3.4 ± 1.1 | 0.9 | 4.0 ± 0.8 | 1.0 |
| MDA-361 | 14 ± 2.3 | 3.5* | 1.9 ± 0.7 | 0.5** |
| SK-BR-3 | 44 ± 6.1 | 7.1* | 9.2 ± 4.8 | 1.5* |
| UACC-812 | 41 ± 7.5 | 10* | 27 ± 5.6 | 6.7* |
| UACC-893 | 66 ± 12 | 32* | 2.3 ± 0.7 | 1.1 |
| ZR-75-1 | 3.3 ± 1.0 | 1.2 | 3.6 ± 0.8 | 1.3 |

*gene amplification of 1.5 or greater;
**physical deletion of less than 0.7.

Of the nine breast cancer cell lines studied, five showed high-level amplification of the HER-2/neu oncogene by FISH. Two of these (UACC-812 and SK-BR-3) showed simultaneous amplification of topoIIα. TopoIIα amplification was found at a low-level of amplification in SK-BR-3, while a high-level of topoIIα amplification was found in UACC-812 cells. The MDA-361 cell line had HER-2/neu amplification with a physical deletion of topoIIα. In the two cell lines with simultaneous amplification of both HER-2/neu and topoIIα (i.e., SK-BR-1 and UACC-812), the copy number of the two genes was not the same. This was unexpected, given the close proximity of these two genes on chromosome 17 and the simple molecular mechanism of amplification of the chromosomal segment carrying these two genes previously suggested (See, Murpy et al., Int. J. Cancer, 64:18 [1996]; and Hoare et al., Br. J. Cancer, 75:275 [1997]), that would yield an identical copy number for the two genes.

Example 2

TopoIIα and HER-2/neu Gene Copy Numbers in Primary Breast Cancer Samples

This example describes the characterization of the copy number for HER-2/neu and topoIIα in primary breast cancer samples. One hundred and thirty-six (136) freshly frozen primary breast tumors were derived from the tumor bank at the University of Lund (Lund, Sweeden). HER-2/neu status was previously determined by Southern blotting in 74 of the primary tumor samples (50 samples with reported amplification and 24 samples with reported normal levels of HER-2/neu). Dual color FISH assays were performed on these samples as described above (See, Example 1), in order to detect the HER-2/neu status of each sample.

FISH detection revealed that 47 of the 50 tumor samples with HER-2/neu amplification as determined by Southern blot also showed amplification by FISH. Also, four low-level HER-2/neu amplifications were identified by FISH in the 24 samples reported to have normal levels of HER-2/neu by Southern Blotting. In the 62 remaining samples, 19 amplifications and one physical deletion were detected by FISH. The total number of HER-2/neu amplifications found, therefore, was 70 out of 136, with an average gene copy number per cell of 21.7±12.2.

The gene copy numbers of topoIIα was then determined by FISH (See, e.g., Example 1) on the 70 primary breast cancer samples determined to have HER-2/neu amplification. Twenty-nine of these tumors (41%) were found to have simultaneous amplification of topoIIα and HER-2/neu (with a mean of 12.7±6.4 and 19.6±10.3 gene copies/cell respectively). In these 29 tumors with amplification of both HER-2/neu and topoIIα, the mean number of HER-2/neu copies was higher than that of topoIIα in 15 tumors (52%), the copy numbers were equal in only 10 tumors (34%), and the topoIIα copy number exceeded the HER-2/neu copy number in 4 tumors (14%). The fact that the copy number of the two genes was not the same in all of the tumor samples (only the same in 34%) was unexpected. This result is unexpected given the close proximity of these two genes on chromosome 17 and the simple molecular mechanism of amplification of the chromosomal segment carrying these two genes.

Example 3

Characterization of TopoIIα-HER-2/neu Amplification by Fiber FISH

This example describes the characterization of topoIIα-HER-2/neu amplification by fiber FISH in the UACC-812 cell line. Mechanically extended DNA fibers were prepared from UACC-812 cells by first embedding the cells in 0.9% agarose (See, Heiskanen et al., *Genomics*, 30:31 [1995]). A small piece of the agarose block was placed on a poly-L-lysine-coated (Sigma) microscope slide and heated on a 95° C. hot plate for 20 seconds. The melted agarose was spread along the microscope slide mechanically with another microscope slide and air dried for 30 minutes. This resulted in the extension of the DNA fibers. The fiber-FISH (for topoIIα and HER-2/neu) was carried out according to the same procedure as described in Example 1 above for FISH. However, proteinase K digestion of the target DNA was omitted and hybridization efficiency was increased by applying denatured probes on the denatured target DNA and re-denaturing them together on a hot plate at approximately 95° C. for 1.5 minutes.

The results of this fiber-FISH analysis revealed that amplified HER-2/neu and topoIIα gene copies were localized exclusively in overlapping clusters in five marker on chromosomes, although chromosomal regions with HER-2/neu signals were also seen. Fiber-FISH was used to characterize the amplicon at high resolution. Surprisingly, HER-2/neu and topoIIα signals were found in separate DNA fibers. Signals for both genes were repeated with themselves, but not with each other, indicating two different tandem repeat-like amplification units. The successive signals for both HER-2/neu and topoIIα were at a constant length from each other, suggesting that the same region was repeatedly amplified. For confirmation of the separate amplicons for HER-2/neu and topoIIα genes, individual nuclei from which separate DNA fibers with either repeated HER-2/neu or topoIIα signals originated were found.

Example 4

TopoIIα Gene Status Does Not Correlate with Immunohistochemistry

This example describes the lack of correlation between topoIIα gene status and immunohistochemical (IHC) detection of protein. In particular, 34 primary breast cancer samples were assayed for topoIIα gene status (employing FISH), and for the presence of topoIIα protein (employing antibody detection). The FISH detection was carried out as described in Example 1. Immunohistochemical analysis started with 5 μm sections of the primary breast cancer samples that were cut and mounted on SUPERFROST slides and dried overnight at 37° C. The sections were then dewaxed and rehydrated. Antigen retrieval of paraffin embedded, formalin fixed tissue sections was done by heating in a microwave for 2–7 minutes in citrate buffer (pH 6.0). TopoIIα monoclonal antibodies Ki-S4 (Kellner et al., *J. Histochem. Cytochem*, 45:251 [1997]) were incubated with the breast cancer sample for 25 minutes at room temperature. The bound antibodies were visualized using a streptavidin-biotin-peroxidase kit (Vector Labs, Burlingame, Calif.) with diaminobenzidine as the chromogen. Methyl green was used for counterstaining. Immunoreaction was quantitated with a CAS200 image analysis system. The obtained scores were tabulated as a percentage of immunopositive nuclei.

The result of the IHC and FISH detection in these breast cancer samples is presented in FIG. 1. The dramatic and unexpected results presented in this Figure indicate that the presence of TopoIIα in the samples as determined by IHC does not correlate with the gene copy status of topoIIα as determined by FISH. FIG. 1 indicates that the presence of topoIIα in the breast cancer samples was essentially independent of topoIIα gene status. In other words, these results demonstrate that topoIIα gene copy number cannot be effectively determined by relying on IHC techniques.

Example 5

HER-2/neu Amplification is Not Significantly Associated with Clinical Response to Chemotherapy This example describes the characterization of HER-2/neu copy number in 191 primary breast cancer tissue samples and the lack of association of HER-2/neu copy number with clinical response to chemotherapy. In particular, the 191 breast cancer tissue samples were obtained from patients who took part in a previously reported prospective randomized trial, where single agent epirubicin chemotherapy was compared with an epirubicin-based combination regimen (CEF—cyclophosphamide, epirubicin, and 5-fluorouracil) as first-line chemotherapy for advanced breast cancer (Joensuu et al., *J. Clin. Oncol.*, 16:3720 [1998]). Briefly, patients eligible for this previous study were required to have distantly metastasized breast carcinoma, with the presence of distant metastases confirmed histologically, cytologically, or radiologically. Patients who had received prior cytotoxic chemotherapy for metastatic disease or anthracyclines in the adjuvant setting were not eligible for the study. Patients with brain or leptomeningeal metastases, those with the World Health Organization (WHO) performance status greater than 2, and those older than 70 years at randomization were also excluded. Clinical examination, imaging and laboratory examinations were carried out before randomization and during follow-up.

In this previous study, patients assigned to combination chemotherapy received CEF (cyclophosphamide 500 mg/m$^2$, epirubicin 60 mg/m$^2$, and 5-fluorouracil 500 mg/m$^2$) intravenously at 3-week intervals as first-line chemotherapy, and MV (mitomycin C 8 mg/m$^2$, combined with vinblastine 6 mg/m$^2$) at 4-week intervals as second-line chemotherapy. Patients assigned to the single agent arm were treated weekly with single-agent epirubicin at 20 mg/m$^2$ as first-line therapy. After disease progression or reaching a maximum cumulative dose of epirubicin, single-agent mitomycin C 8 mg/m$^2$ was given 4 times weekly as second-line therapy. Local radiotherapy for painful metastatic lesions, bisphosphonate therapy, and anti-nausea medication were allowed at any time during the study. Responses to first-line chemotherapy were evaluated during regular follow-up visits to the oncology clinic. The clinical response was classified into 4 categories; "complete response" (CR), "partial response" (PR), "no change in disease progression" (NC), and "progressive disease" (PD) according to the WHO criteria (Miller et al., Cancer, 47:207–214 [1981]).

The response rates, reported in this previous study, to CEF (CR+PR, 55%) and to single-agent epirubicin (CR+PR, 48%) were statistically not different (p=0.21) in this trial, and overall survival was also similar. Because epirubicin was the only topoisomerase II inhibitor agent in both first-line treatments and because its cumulative dose was similar in both arms (471 mg/m$^2$ in the CEF arm and 444 mg/m$^2$ in the single-agent epirubicin arm), the two treatment groups were combined and analyzed as a single group for predictive correlations in the present example. Of the 303 patients randomized in the trial, archival paraffin-embedded and histopathologically representative samples (containing >50% carcinoma cells) from the primary tumor were available from 196 patients. HER-2/neu FISH was carried out on 191 of these samples as described below.

FISH was performed using a digoxigenin-labeled probe for HER-2/neu obtained from Zymed Inc. (South San Francisco, Calif.). Pretreatment of paraffin sections was carried out using a SPoT-LIGHT FFPE reagent kit from Zymed Inc. Briefly, sections were de-paraffinized and incubated in Pretreatment Buffer in a temperature-controlled microwave oven (at 92° C. for 10 min). Enzymatic digestion was carried out with FFPE digestion enzyme (10 to 40 min at room temperature). The slides were washed with PBS and dehydrated in graded dilutions of ethanol. The HER-2/neu probe was then applied to the slides. The slides were denatured on a hot plate (94° C.) for 3 min and hybridized overnight at 37° C. After hybridization, the slides were stringency washed with 0.5×SSC (5 min at 75° C.), followed by three washes in PBS/0.2% Tween20. The HER-2/neu probe was detected with anti-digoxigenin rhodamine (diluted 1:300, Roche-Boehringer, Mannheim, Germany). Nuclei were counterstained with 0.1 μM 4,6-diamidino-2-phenylindole (DAPI) in an antifade solution (Vectashield, Vector Laboratories, Burlingame, Calif.).

Hybridizations were evaluated using an Olympus BX50 epifluorescence microscope. Signals from at least 50 to 200 non-overlapping nuclei with intact morphology were evaluated to determine the mean number of signals/cell for each probe. Absolute copy numbers for HER-2/neu were then determined. Amplification of HER-2/neu was defined, in this example, as the presence of 6 or more copies of HER-2/neu in over 50% of nuclei. All analyses were carried out in a blinded fashion (i.e. without knowing the clinical response or survival). HER-2/neu gene amplification, as defined in this example, was observed in 61 of the 191 tumors tested (i.e., 31.9%).

Amplification of HER-2/neu was found to be associated with a negative hormone receptor status and p53 overexpression, but there was no significant association between the presence of HER-2/neu amplification and the primary tumor size, axillary lymph node status or the dominant site of metastasis. HER-2/neu amplification was significantly associated with a short distant disease-free interval, and overall cancer-specific survival.

In regards to HER-2/neu status and previously reported response to epirubicin-based chemotherapy, no significant correlation was found. A comparison of HER-2/neu status and response to epirubicin-based chemotherapy is presented in Table 2.

TABLE 2

Association of HER-2/neu Gene Status and Response to Chemotherapy

| Response to Chemotherapy | Complete response | Partial response | No change | Progressive disease | Not evaluable |
|---|---|---|---|---|---|
| No HER-2/neu amplification | 6 (4.6%) | 61 (47%) | 36 (28%) | 23 (18%) | 4 (3%) |
| HER-2/neu amplification | 7 (11%) | 18 (30%) | 11 (18%) | 18 (30%) | 7 (11%) |

These results demonstrate that there is no significant correlation between the HER-2/neu amplification status and the clinical response to first-line chemotherapy. This is evidenced by the fact that the prevalence of HER-2/neu amplification was not significantly different between responders (CR or PR) and non-responders (NC or PD) (p=0.42).

Example 6

Predictive Value of TopoIIα and HER-2/neu Amplification in Primary Tumors Cells—FISH TopoIIα Detection This example describes the predictive value of dual amplification of topoIIα and HER-2/neu in regards to clinical response to topoisomerase II inhibitor chemotherapy. In particular, FISH was used (as described in Example 5) to determine the topoIIα gene copy number for the 61 tumor samples (i.e., primary cells) determined to have HER-2/neu amplification in Example 5 (See, Table 2).

PAC clones probe for topoIIα were obtained by PCR-based screening of a PAC library. A chromosome 17 pericentromeric probe (p17H8) was used as a reference probe to determine the overall copy number of chromosome 17. The specificity of the topoIIα probe was confirmed by PCR with topoIIα specific primers. This topoIIα probe does not contain HER-2 DNA sequence since there is no amplification using 3 pairs of HER-2 specific primers covering 5' end, middle, and 3' end of HER-2. The PCR-analysis showed that the topoIIα probe did not recognize sequences from HER-2/neu. The pericentromeric probe for chromosome 17 was labeled with fluorescein-5-dUTP and the topoIIα probe with digoxigenin-11-dUTP by standard nick-translation. A mixture of the topoIIα and 17 centromere probes (30 ng and 10 ng, respectively) was diluted in 10 μl of hybridization buffer (2× standard saline citrate (SSC), 50% formamide, 10% dextran sulfate), and applied to the slides under coverslips.

In this Example, control hybridizations to non-malignant breast tissue and normal peripheral blood lymphocytes were also carried out to ascertain the relative hybridization efficiencies of topoIIα and 17 centromere. The sensitivity of FISH in the detection of aberrations of topoIIα when using paraffin sections was validated with a separate set of 15 tumors in which freshly frozen tumor material had been analyzed previously by FISH. TopoIIα amplification was defined, in this example, as a copy number ratio of 1.5 or more, and deletion was defined, in this example, as a ratio of 0.7 or less TopoIIα amplification (as defined in this Example) was found in 21 (34%) tumors, 27 (44%) had no topoIIα copy number alterations, and 13 (21%) showed topoIIα deletion (as defined in this example). The median number of topoIIα gene copies per cell in tumors with amplification was 14 (the median number for HER-2/neu gene copies was 25/cell). In tumors with topoIIα deletion, the median number of gene copies was 2.3 (4.3 for chromosome 17 centromere; the average copy number ratio was 0.53).

In regards to topoIIα gene status in HER-2/neu positive breast cancer samples and previously reported response to epirubicin-based chemotherapy, a significant correlation was found. A comparison of topoIIα gene status in the HER-2/neu positive samples (gene amplification) and response to epirubicin-based chemotherapy is presented in Table 3.

TABLE 3

Association of TopoIIα Gene Aberrations with Clinical Response To Chemotherapy in 61 HER-2/neu Positive Breast Cancer Samples

| Response to Chemotherapy | Complete response | Partial response | No change | Progressive disease | Not evaluable |
|---|---|---|---|---|---|
| TopoIIα amplification | 7 | 8 | 2 | 2 | 2 |
| Unaltered | 0 | 8 | 5 | 10 | 4 |
| TopoIIα Deletion | 0 | 2 | 4 | 6 | 1 |

These results indicate that topoIIα aberrations were strongly associated with clinical response to first-line epirubicin-based chemotherapy. Significantly, all seven patients who had a complete response to anthracycline chemotherapy had a primary tumor with topoIIα and HER-2/neu amplification. Fifteen (79%) of the 19 evaluable patients with topoIIα and HER-2/neu amplification achieved either a complete or partial response to chemotherapy (i.e., were identified as suitable for treatment with topoisomerase II inhibitors). In contrast, only 8 of the 23 (35%) evaluable patients with an unaltered topoIIα status and 2 of the 12 (17%) patients who had cancer with topoIIα deletion responded to epirubicin-containing chemotherapy. Also, the duration of response was significantly longer in patients with topoIIα amplification than in those with deletion or with unaltered topoIIα (median 10 vs. 5 months, p=0.01).

TopoIIα alterations were not associated with the length of long term disease-free survival following breast surgery, (i.e., not influenced by chemotherapy that was given for metastatic disease). In agreement with the association to favorable clinical response, topoIIα amplification together with HER-2/neu amplification was significantly associated with improved post-chemotherapy survival as compared to patients who had cancer with an unaltered topoIIα gene copy number or topoIIα deletion (median 20 vs. 11 months).

Example 7

Chromogenic In Situ Hybridization (CISH) Detection of HER-2/neu

This example describes chromogenic in situ hybridization (CISH) detection of HER-2/neu in primary breast cancer samples, as well as a comparison between CISH, FISH, and IHC detection of HER-2/neu gene copy number or HER-2 protein. One-hundred and fifty-seven (157) tumor samples were employed in this example, and were collected prospectively at the Jules Bordet Institute.

CISH was performed on 5 mm thick archival formalin-fixed paraffin-embedded tissue sections. In brief, the sections were de-paraffinized and incubated in pretreatment buffer in a temperature-controlled microwave oven (at 92° C. for 15 minutes, using a SPoT-LIGHT FFPE reagent kit from Zymed Inc., (South San Francisco, Calif.). The sections were then washed three times with deionized water. Enzymatic digestion was done by applying 100 μl of FFPE digestion enzyme on to slides (10–15 min at room temperature). The slides were then washed with PBS and dehydrated with graded ethanols. The ready-to-use digoxigenin-labeled HER-2/neu probe (Zymed, consisting of two contig BAC clones) was applied onto slides which were covered under 14×14 mm coverslips (10 μl probe mixture/slide). The slides were denatured on a hot plate (94° C.) for 3 min, and the hybridization was carried out overnight at 37° C. After hybridization, the slides were washed with 0.5×SSC (standard saline citrate; 5 min at 75° C.), followed by three washes in PBS/0.025% Tween20 (at room temperature). The HER-2/neu probe was detected with sequential incubations with anti-digoxygenin-fluorescein, anti-fluorescein-peroxidase and diaminobenzidine according to manufacturer's instructions (Zymed Inc.). Tissue sections were lightly counterstained with hematoxylin and embedded.

The CISH hybridizations were evaluated using an Olympus BX50 microscope equipped with 40× and 60× dry objectives using 10×22 widefield oculars. Unaltered gene copy number was defined, in this example, as 1 to 5 signals per nucleus. Low level amplification was defined, in this example, as 6 to 10 signals per nucleus in over 50% of cancer cells, or when a small gene copy cluster was found. Amplification of HER-2/neu was defined, in this example, when a large gene copy cluster in over 50% of carcinoma cells, or numerous (>10) separate gene copies were seen. Images were captured using a Pixera PVC100C digital camera (Pixera Corp., Los Gatos, Calif.).

In this example, FISH was done as previously described (Grancberg, et al., Am. J. Clin. Pathol., 113:675 [2000]). In brief, a fresh tumor sample of 0.5 cm³ of a freshly made imprint touch preparation were obtained immediately after surgery. Cells from tumor pieces were mechanically disintegrated, centrifuged and treated with 0.075M KCl for 1 h at 37° C. After washing in methanol:acetic acid (3:1), the cells were spread onto microscope slides. The slides were denatured in 70% formamide/2×SSC (pH 7) at 73° C. for 10 min. After dehydration in an ethanol series, 10 μl of the probe (LSI HER-2/CEP17, Vysis Inc., Downers Grove, Ill.) was denatured (73° C. for 5 min) and applied onto slides. The hybridization was carried out overnight at +37° C. in a moist chamber. The samples were washed in 0.4×SSC (at 73° C., 2 min), followed by 0.4×SSC/0.1% Nonidet P-40 (2 min at room temperature) to remove excess probes. Nuclei were counterstained with 4',6-diamino-2 phenylindole dihydrochloride (DAPI, 1 mg/ml) in an antifade embedding solution (p-phenylene-diamine dihydrochloride).

Hybridization signals were enumerated in at least 150–250 morphologically intact and non-overlapping nuclei. A Leica DMRB epifluorescence microscope equipped with a 100× oil immersion objective and a triple bandpass filter was employed for simultaneous detection of Spectrum Green, Spectrum Orange and DAPI (filter from ChromaTechnology, Tucson, Ariz.). Her-2/neu amplification was determined as a ratio of HER-2/neu and chromosome 17 centromere signal counts. Ratios below 2 were defined, for this example, as "no amplification," those between 2 and 5, were defined for this example, as "low level amplification," and those above 5, were defined for this example, as "high level amplification."

Immunohistochemistry (IHC) of HER-2 was done on tissue sections adjacent to those used in the CISH detection described above. The sections were de-paraffinized followed by antigen-retrieval in 0.01 M citrate buffer (pH 7.3, 94° C. for 20 min, using a temperature-controlled microwave oven). After blocking for non-specific antibody binding (using the blocking reagent HISTOSTAIN PLUS kit), the sections were incubated overnight (at 4° C.) with a monoclonal antibody to the intracellular domain of HER-2 protein (clone CB-11, Novocastra Laboratories, Newcastle UK). A standard avidin-biotin-peroxidase complex (ABC) technique was used for visualization, with diaminobenzidine as the chromogen (HISTOSTAIN PLUS-kit, Zymed Laboratories, San Francisco, Calif.). Intense cell membrane immunoreaction present in over 50% of cancer cells was designated as "3+" staining and was considered as overexpression of HER-2. Staining present in a smaller proportion of cells or that with lower intensity was designated as "2+" staining. The controls consisted of three cell lines (SK-BR-3; >30 gene copies of HER-2/neu, MDA-MB-453; 8 gene copies of HER-2/neu, and ZR-75-1, 2 gene copies of HER-2/neu) were fixed overnight with 10% formalin and pelleted as a normal paraffin block.

Results obtained by CISH and FISH performed on cells prepared from a fresh tumor sample were correlated. In a series of 157 unselected breast cancers, the prevalence of HER-2/neu amplification was determined to be 23.6% by FISH and 17.2% by CISH. There were 120 tumors with no amplification and 27 with amplification by both methods (Table 4). FISH identified HER-2/neu amplification in 10 tumors which were negative by CISH (5 gene copies or less) (Table 4). The kappa coefficient (measuring agreement between the methods, 0=no agreement, 1=perfect agreement) was 0.81 (95% confidence interval 0.69–0.92).

TABLE 4

Comparison Between CISH and FISH Detection of HER-2/neu Copy Number

|  | CISH - No amplification | CISH - Amplification |
|---|---|---|
| FISH - No amplification | 120 (76.4%) | 0 (0%) |
| FISH - Amplification | 10 (6.4%) | 27 (17.2%) |

HER-2/neu gene amplification by CISH and FISH was also compared with HER-2 protein overexpression detected by immunohistochemistry (using monoclonal antibody CB-11) (Table 5). Immunohistochemistry was somewhat less sensitive but generally in good agreement with FISH and CISH. The prevalence of HER-2 overexpression was 19.7% as determined by immunohistochemistry. There were 11 tumors positive by FISH but negative by IHC, but only 2 such tumors positive by CISH. Only one of the immunohistochemically weakly positive (2+) tumors were found to be amplified using CISH or FISH.

TABLE 5

FISH and CISH HER-2/neu Analysis Compared to IHC HER-2 Analysis

|  | IHC - Negative (0 or +1) | IHC - Weakly positive (2+) | IHC - positive (3+) |
|---|---|---|---|
| FISH - No amplification | 115 | 4 | 1 |
| FISH - Amplification | 11 | 1 | 25 |
| CISH - No amplification | 124 | 5 | 1 |
| CISH - Amplification | 2 | 0 | 25 |

As described above, the agreement between CISH with FISH was generally very good. However, there were 10 tumors (6.4%) defined, in this example, as amplified by FISH but not amplified (as defined in this example) by CISH (See, Table 4). One explanation for this difference is the sample materials. FISH was done on fresh tissue material, whereas CISH was conducted using paraffin-embedded samples, which are technically more difficult to hybridize. A second explanation, examining the discordant tumors in detail (See Table 6), it appears that all but one tumor (that was negative by CISH) was scored as having a borderline 'low level' amplification in FISH (copy number ratio 2 to 5). Moreover, eight of these tumors were negative by immunohistochemistry (one had 2+ staining). Thus, the discepencies may simply reflect the fact that the threshold for determining low level amplification as used in this example may not always clearly detect HER2 overexpression.

TABLE 6

Results of HER-2/neu CISH, FISH, and IHC in Cases with Disagreement

| Tumor No. | FISH | CISH | IHC |
|---|---|---|---|
| #22 | Low level amplification | Not amplified | Negative (0 or 1+) |
| #41 | Low level amplification | Not amplified | Negative (0 or 1+) |
| #52 | Low level amplification | Not amplified | Negative (0 or 1+) |
| #54 | Low level amplification | Not amplified | Negative (0 or 1+) |
| #88 | High level amplification | Not amplified | Negative (0 or 1+) |
| #106 | Low level amplification | Not amplified | Weakly positive (2+) |
| #123 | Low level amplification | Not amplified | Negative (0 or 1+) |
| #126 | Low level amplification | Not amplified | Negative (0 or 1+) |
| #127 | Low level amplification | Not amplified | Negative (0 or 1+) |
| #135 | Low level amplification | Not amplified | Negative (0 or 1+) |

Example 8

Exemplary TopoIIα Probe and Other TopoIIα Probes

This Example describes an Exemplary TopoIIα probe useful for detecting TopoIIα copy number in, for example, FFPE tissue sections, fresh tissue sections, cell preparations, and metaphase chromosome spreads using in situ hybridization detection methods such as FISH and CISH. This Example also describes procedures for constructing similar probes.

The Exemplary TopoIIα probe described in this Example is available from Zymed Laboratories (South San Francisco, Calif., Cat. No. 84-0600). The nucleic acid sequence of the Exemplary TopoIIα probe is an approximately 170 kb sequence from human chromosome seventeen (17) that encompasses the TopoIIα gene, but does not contain the HER2/neu gene. FISH experiments revealed that the probe binds specifically to the topoIIα gene locus on chromosome band 17q11–21 and absence of chimerism. PCR with HER2/neu specific primers demonstrated that the sequence of the Exemplary TopoIIα probe does not contain the HER2/neu gene.

Sequencing the ends of the Exemplary probe revealed that this sequence is bounded on the 3' end by the sequence shown in FIG. 2A (SEQ ID NO:9), and bounded on the 5' end by the sequence shown in FIG. 2B (SEQ ID NO:10). Comparison with the published human genome sequence in chromosome 17q 11–21 region in Gene Bank revealed that the sequence of the Exemplary probe is located about 500 kb downstream of the HER2/neu gene.

The sequence of the Exemplary probe may be constructed, for example, by employing the 3' and/or 5' ends of the Exemplary probe sequence (i.e. SEQ ID NOS:9 and 10). For example, these sequences may be used to screen a library of human sequences, such that a clone containing this sequence is found and isolated. This clone can be further manipulated by standard molecular biology techniques such that sequences similar to, or identical to, the Exemplary probe sequence are generated. SEQ ID NOs:9 and 10 may also be employed to screen human gene sequence databases (e.g. at chromosome 17) such that the sequences between SEQ ID NOs:9 and 10, and near SEQ ID NOs:9 and 10, may be determined (and then used to generate sequences that are the same or similar to the Exemplary probe sequence using standard molecular biology techniques). Preferably, if sequences similar to the Exemplary probe sequence are generated, the length of the resulting sequence is selected such that it is between 100 kb and 1 megabase and is capable of hybridizing to human chromosome 17 (e.g., at a region that contains the TopoIIα gene and not the HER2/neu gene).

To confirm that the Exemplary probe contained the TopoIIα gene sequence, a PCR test was conducted. In particular, the Exemplary probe sequence was used as a template and Two topoIIα primers were used (TopoIIαA: 5-'GCC TCC CTA ACC TGA TTG GTTA-3', SEQ ID NO:11; and TopoIIαB: 5'-CTC AAG AAC CCT GAA AGC GACT-3', SEQ ID NO:12). The PCR reaction was performed in a volume of 25 μl containing 100 ng of Tracer DNA, 20 pmols of each primer, 1× KLENTAQ DNA polymerase (Clonetech), and 200 μM of each dNTPs (Roche). The PCR was performed for 30 cycles of 94 degrees Celsius for 1 minute. The resulting gel revealed a clear TopoIIα PCR product (259 bases). This same type of PCR test may be used on other TopoIIα probe sequences that are generated to confirm that the TopoIIα gene is encompassed by the probe.

The Exemplary probe is labelled with digoxigenin (DIG). The Exemplary probe sequence, or other probes with the same or similar sequences, can be labelled with any type of detectable label (e.g., such that the probe can be detected during in situ hybridization procedures such as FISH or CISH). Also, the Exemplary probe's specificity has been demonstrated by CISH detection methods (data not shown) on the mammary gland adenocarcinoma MCF-7 (ATCC# HTB-22) which does not have TopoIIα gene amplification or deletion, and mammary gland adenocarcinoma cells MDA-MB-361 cell (ATCC# HTB-27), which has the TopoIIα gene deleted.

Example 9

In Situ Hybridization Methods with the Exemplary TopoIIα Probe

This example describes in situ hybridization methods (CISH and FISH) that may be used with TopoIIα probes, such as the Exemplary TopoIIα Probe described in Example 8. In particular, this Example describes in situ hybridization methods with the Exemplary probe in Formalin-Fixed, Paraffin-Embedded (FFPE) Tissue Samples, as well as Cell Sample/Metaphase Chromosome samples. Finally, this example describes a quality control procedure that may be used with any of these methods.

A. Single-Color CISH for Detection of DIG Labeled Exemplary TopoIIα Probe on FFPE Tissue Sections I. Pretreatment 1. Deparaffinization

| | |
|---|---|
| Xylene | 10 Min × 2 |
| 100% EtOH | 5 Min × 3 |
| Air dry slides | |

2. Heat treatment
(boil the slide by using microwave with temperature probe, or pressure cooker or hot plate)

| | |
|---|---|
| Tris-EDTA buffer, pH 7.0 (SP.T-Light Tissue Heat Pretreatment Buffer, Cat.# 00-8401) | 15 Min, 96–100° C. |
| dH₂O | 2 Min × 3 |

3. Pepsin digestion:
   Pepsin at 37° C. 3 Min.
Note: different concentrations of pepsin and incubation times (1–10 min) may be required depending on tissue fixation and type of tissue. Excessive digestion will cause loss of nuclei and chromosome structure, while inadequate digestion may result in loss of signal.
   dH₂O 2 min×3
4. Dehydration with graded alcohol

| | |
|---|---|
| 70% EtOH | 2 min |
| 85% EtOH | 2 min |
| 95% EtOH | 2 min |
| 100% EtOH | 2 min |
| 100% EtOH | 2 min |

5. Air dry slides
6. Label slides with pencil
II. Option 1: Co-denaturation and Hybridization:
(use PCR machine with slide block, or heating block with temperature digital display and humidity slide chamber and 37° C. incubator)
1. Add probe: add 12–15 μl of probe to the center of 22×22 mm coverslip, or 20 μl of probe to the center of 24×32 mm coverslip.
2. Coverslip: coverslip slide at appropriate tissue sample area.
3. Seal with rubber cement: seal edges of coverslip with thin layer of rubber cement for preventing evaporation during incubation.
4. Denaturation at 94° C. for 5 min: place the slides in a slide block of PCR machine, or on a heating block with temperature digital display.
5. Incubation at 37° C. overnight: leave the slides in the slide block of PCR machine or place the slides in a dark humid box in a incubator.
Option 2: Separate Denaturation (When PCR Machine or Heating Block Are not Available)

1. Denature tissue in fresh made denaturing buffer at 75° C. 5 min.
Denaturing buffer: 4 ml 20×SSC (20×SSC buffer=0.3M Sodium Citrate, with 3M NaCl, ph 7.0), 8 ml ddH$_2$O, 28 ml formamide.
(For more than one slide samples, add 1° C. per slide. For example, if 2 slides are used, set temperature to 76° C.).
2. Dehydration with graded alcohol

| | |
|---|---|
| 70% EtOH | 2 min, at −20° C. |
| 85% EtOH | 2 min, at −20° C. |
| 95% EtOH | 2 min, at −20° C. |
| 100% EtOH | 2 min, at RT |
| 100% EtOH | 2 min, at RT |

3. Air dry slides. At the same time process step 4.
4. Denature labeled probe 75° C., 5 min.
5. Place denatured probe in ice immediately.
6. Add probe: add 12–15 μl of denatured probe to the center of 22×22 mm coverslip.
7. Coverslip slides at appropriate tissue sample area.
8. Incubation: place slides in a dark humid box at 37° C. for overnight (more than 14 hours).

III. Stringency Wash:
1. After hybridization, carefully remove rubber cement and coverslip.
2. Stringency wash: Wash slides in 0.5×SSC at 75° C. for 5 min.
(Add 1° C. per slide for more than 2 slides, but do not go higher than 80° C.)
3. dH$_2$O wash: 2 min×3

IV. Immunodetection:
1. 3% H$_2$O$_2$ in absolute Methanol: (for Peroxidase Quenching) 10 min
2. 1×PBS (10 mM)/Tween 20 (0.025%) wash: 2 min×3
3. Add blocking reagent 2 drops/slide at RT (CAS-Block; 0.25% casein, 0.2% gelatin, and 10 mM PBS, pH 7.4) 10 min
   Note: use enough reagents to cover all the area of tissue.
4. Blot off blocking reagent, DO NOT RINSE.
5. Add FITC-anti-dig antibody 2 drops/slide at RT 45 (30–60) min
   Note: use enough reagents to cover all the area of tissue.
6. 1×PBS/Tween 20 (0.025%) wash 2 min×3
If FISH is desired, add 1 drop of VECTASHIELD Mounting Medium with DAPI (Vector, Cat. No. H-1200) on the section, then coverslip. Incubate for 10 min at RT in a dark chamber box before performing fluorescent microscopy. After analysis is done, remove coverslip, wash slide in 1×PBS/Tween 20 (0.025%) 3 times, each time 2 min. Continue to next step.
7. Add HRP-anti-FITC 2 drops/slide at RT 45 (30–60) min
   Note: use enough reagents to cover all the area of tissue.
8. PBS/Tween (0.025%) wash 2 min×3
9. Add DAB, 3 drops/slide, 30 min
   Note: use enough reagents to cover all the area of tissue.
(Make DAB by adding 1 drop of each reagent A (CAS-BLOCK), B (FITC-Sheep anti-Digoxigenin) and C(HRP-Goat anti-FITC) to 1 ml dH$_2$O, then mix well)
10. Wash with running tap water: 2 min.

V. Counterstaining and Coverslipping
1. Counterstain with hematoxylin 6 sec–1 min.
Time of counterstaining is dependent on tissues used. Dark counterstaining is not recommended as it may obscure the positive signal.
2. Wash with running tap water 2 min
3. Dehydrate with graded EtOH
   (70%, 85%, 95%, 100%, 100%) 2 min each
4. Xylene 2 min×2
5. Coverslip with Histomount (Cytoseal 6.0, cat. #8310-16, Stephen Scientific).

V. Microscopy
Visualize probe in cells.

B. Cell Sample or Metaphase Chromosome Sample
Fix cell sample on HISTOGRIP or SUPERFROST PLUS coated (or other) glass slide.
Pretreatment
1. Immerse slides in 2×SSC buffer (20×SSC buffer=0.3M Sodium Citrate, with 3M NaCl, ph 7.0) at 37 degrees Celsius for 60 minutes.
2. (Optional) Pretreat cells with SP•T LIGHT Cell Pretreatment Reagent (or other Pepsin composition in acidic buffer) for 5 minutes at 37 degrees Celsius. Incubation time may be from 1–10 minutes depending on cell type and slide-making conditions. Excessive pepsin digestion will cause loss of nuclei and chromosome structure. Inadequate digestion may result in loss of signal.
3. Wash in dH$_2$O for 3×2 minutes at room temperature (RT).
4. (Optional) Immerse slides in 10% bufferred formalin for 1 minute at RT.
5. Wash in dH$_2$O for 3×2 minutes at RT.
6. Dehydrate slides in 70%, 85%, 95%, and 100% ethanol for 2 minutes each, and then air dry.
Slides are now ready for ISH procedure (alternatively, slides can be stored in 70% ethanol at −20 degrees Celsius.

Denaturation and Hybridization
1. Add 15 μl of Exemplary topoIIa probe (probe) to the center of the sample and cover with a 22×22 mm coverslip (use more probe for bigger sample and larger coverslip).
2. Seal edges of coverslip with thin layer of rubber cement to prevent evaporation of probe solution during incubation.
3. Denature the slides on a hot plate or slide warmer at 80 degrees Celsius for 3 minutes (2–5 minute range), or in the slide block of a PCR thermal cycler.
4. Place slide in a dark humidity box or in the slide block of a PCR thermal cycler for 16–24 hours at 37 degrees Celsius.

Stringency Wash
1. Remover rubber cement and coverslip.
2. Immerse slides in 0.5×SCC buffer, using a Coplin jar, for 5 minutes at 72 degrees Celsius (note—this temperature is based on one slide, but each slide causes a 1 degree Celsius drop in solution temperature. Therefore, if there is more than one slide, adjust the water bath temperature accordingly. For example, if washing 4 slides, adjust the water bath temperature to 75 degrees Celsius. Do not go higher than 80 degrees Celsius.).
3. Wash slides in PBS/Tween 20 buffer (1 part Tween-20, 3900 parts 0.1 M PBS) for 3×2 minutes at RT.

Perform Immunodetection and Counterstaining-Coverslipping as described above in part A above.

C. Quality Control Procedures
Quality control over the accuracy of the above procedures may be assured by using some or all of the controls described below.
   Positive (Amplification) Tissue Control: External positive control materials for clinical research should be fresh autopsy/biopsy/surgical specimens fixed, processed, and embedded as soon as possible in the same manner as the patient sample(s). Specimens processed differently from the specimen sample(s) validate reagent performance, and do not verify tissue preparation. Positive tissue controls are indicative of correctly prepared tissues and proper staining techniques. One positive tissue control for each set of test conditions should be included in each run.

Tissues used for the positive control materials should be selected from specimens with well-characterized levels of TopoIIα gene. Approximately 5–10% of breast cancer tissue has TopoIIα gene amplification and may be a useful source of positive control tissue.

Known positive controls should be utilized for monitoring the correct performance of processed tissues and test reagents, rather than as an aid in interpreting sample results. If the positive tissue controls fail to demonstrate positive staining, results with the specimen samples should be considered invalid.

Negative or Normal (Diploid) Tissue Control: Human diploid tissue samples normally have two TopoIIα gene copies in each cell. Therefore, a true negative tissue sample is not available. However, normal tissue can be used as a negative control for gene amplification or deletion. Use a negative tissue control (known to be diploid) fixed, processed, and embedded in the same manner as the sample (s) with each staining run. This will verify the specificity of the ISH probe, and provide an indication of non-specific background staining (false positive staining).

A negative tissue control that is separate from the sample is known as an 'external' negative control. If an external negative tissue control is not available then a normal section of the sample can serve as an 'internal' negative tissue control.

Reagent (No-Probe) Control: A reagent control is run on a section of sample specimen without the probe. The reagent control is useful in evaluating the possibility of nonspecific staining, particularly when performing ISH in tissue sections. The reagent control should be stained in the same way as the test samples except that hybridization buffer, that does not contain the probe, should be used during the hybridization step. Slide pretreatment, denaturation, and immunodetection should be performed under the same conditions as test samples.

Example 10

Predictive Value of TopoIIα and HER-2/neu Amplification in Primary Tumors Cells—CISH TopoIIαDetection This example describes the predictive value of dual amplification of topoIIα and HER-2/neu in regards to clinical response to topoisomerase II inhibitor chemotherapy. In particular, CISH was used to determine the topoIIα gene copy status for the same primary tumor (breast cancer) patient samples determined to have HER-2/neu amplification as described in Example 6. However, the paraffin block material was exhausted for 16 tumors, so only 45 patient samples were used in this Example, instead of the full 61 tumor samples tested by FISH in Example 6 (See, Table 3).

Slides were de-paraffinized and incubated in 0.1 M Tris-HCl (pH 7.3) in a temperature-controlled microwave oven (at 92 degrees Celsius for 10 minutes, followed by cooling down for 20 minutes at room temperature). After a wash with PBS, enzymatic digestion was done by applying 100 µl of digestion enzyme on to slides for 10–15 min at room temperature (Digest-All III solution, which is a 0.25% pepsin enzyme solution, sold by Zymed Inc., South San Francisco, Calif.). The slides were then washed with PBS and dehydrated with graded ethanols. The ready-to-use digoxigenin-labeled DNA probe for topo IIα (i.e. the Exemplary topoIIα probe described in Example 8, available from Zymed Labs.) was applied onto slides which were covered under 18×18 mm coverslips (10 µl probe mixture/slide). The slides were denatured on a thermal plate (at 94 degrees Celsius for 3 minutes), and the hybridization was carried out overnight at 37 degrees Celsius. After hybridization, the slides were washed with 0.5×SSC (standard saline citrate; 5 min at 75C), followed by three washes in PBS. The results of this Example are shown in Table 7 below. A comparison of the results using FISH (table 3) and CISH (table 7) to detect topoIIα status is presented in table 8 below.

TABLE 7

Association of TopoIIα Gene Aberrations with Clinical Response To Chemotherapy in 45 HER-2/neu Positive Breast Cancer Samples

| Response to Chemotherapy | CR or PR | NC or PD | Not evaluable | Total |
| --- | --- | --- | --- | --- |
| TopoIIα Amplification | 7 | 16 | 3 | 29 |
| No Amplification | 12 | 4 | 3 | 19 |
| Total | 19 | 20 | 6 | 45 |

P-value = 0.0095 (excluding "NE" = response not evaluable);
CR = complete response
PR = partial response;
NC = no change in disease status;
PD = progressing disease.

TABLE 8

Comparison of TopoFish (Table 3) v. TopoCish (Table 7)

| topoCISH | topoFISH normal-or-del | amp | TOTAL |
| --- | --- | --- | --- |
| no amp | 25 | 1 | 26 |
| amp | 4 | 15 | 19 |
| TOTAL | 29 | 16 | 45 | kappa coefficient k = 0.767 (considered as "excellent agreement")

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in medicine, immunology, chemistry, and molecular biology or related fields are intended to be within the scope of the following claims.

We claim:

1. A method for identifying a candidate for topoisomerase II inhibitor treatment, comprising:
   a) providing a sample of breast cancer cells from a candidate subject;
   b) detecting a copy number for HER-2/neu and topoIIα in said breast cancer cells; and
   c) identifying said candidate subject as suitable for treatment with a topoisomerase II inhibitor, wherein said identifying comprises demonstrating amplification of said copy number for said HER-2/neu and said topoIIα, wherein said amplification indicates said candidate subject is suitable for topoisomerase II inhibitor treatment.

2. The method of claim 1, wherein said demonstrating comprises comparing said copy number of said HER-2/neu to a control copy number, and comparing said copy number of said topoIIα to said control copy number.

3. The method of claim 2, wherein said copy number of said HER-2/neu is at least 1.5 times greater than said control copy number.

4. The method of claim 2, wherein said copy number of said topoIIα is at least 1.5 times greater than said control copy number.

5. The method of claim 1, wherein said detecting further comprises contacting said sample of breast cancer cells with a first probe specific for said HER-2/neu and a second probe specific for said topoIIα.

6. The method of claim 5, wherein said second probe comprises at least about 100,000 nucleotides.

7. The method of claim 1, wherein said detecting comprises in situ hybridization.

8. The method of claim 6, wherein at least one of said probes is detected by chromogenic in situ hybridization.

9. A method for identifying a candidate for topoisomerase II inhibitor treatment, comprising:
   a) providing a sample of breast cancer cells from a candidate subject, wherein said breast cancer cells comprise an amplified copy number for HER-2/neu,
   b) detecting a copy number for topoIIα in said breast cancer cells; and
   c) identifying said candidate subject as suitable for treatment with a topoisomerase II inhibitor, wherein said identifying comprises demonstrating amplification of said copy number for topoIIα, wherein amplification of both said HER-2/neu and said topoIIα indicates said candidate subject is suitable for topoisomerase II inhibitor treatment.

10. The method of claim 9, wherein said demonstrating comprises comparing said copy number of said topoIIα to a control copy number.

11. The method of claim 10, wherein said copy number of said topoIIα is at least 1.5 times greater than said control copy number.

* * * * *